(12) United States Patent
Hall

(10) Patent No.: US 11,885,771 B2
(45) Date of Patent: Jan. 30, 2024

(54) MEASUREMENT PROBE

(71) Applicant: RENISHAW PLC, Wotton-Under-Edge (GB)

(72) Inventor: Liam Hall, East Lothian (GB)

(73) Assignee: RENISHAW PLC, Wotton-Under-Edge (GB)

( * ) Notice: Subject to any disclaimer, the term of this patent is extended or adjusted under 35 U.S.C. 154(b) by 53 days.

(21) Appl. No.: 17/552,037

(22) Filed: Dec. 15, 2021

(65) Prior Publication Data

US 2022/0178885 A1   Jun. 9, 2022

Related U.S. Application Data

(63) Continuation of application No. 15/510,791, filed as application No. PCT/GB2015/052814 on Sep. 29, 2015, now Pat. No. 11,231,398.

(30) Foreign Application Priority Data

Sep. 29, 2014 (GB) ..................... 1417164

(51) Int. Cl.
*G01N 29/34* (2006.01)
*G01B 5/012* (2006.01)
(Continued)

(52) U.S. Cl.
CPC ......... *G01N 29/343* (2013.01); *A61B 8/4254* (2013.01); *G01B 5/012* (2013.01);
(Continued)

(58) Field of Classification Search
None
See application file for complete search history.

(56) References Cited

U.S. PATENT DOCUMENTS

| 3,921,442 A | 11/1975 | Soloway |
| 4,334,433 A | 6/1982 | Takahashi et al. |

(Continued)

FOREIGN PATENT DOCUMENTS

| CN | 2203441 Y | 7/1995 |
| CN | 1185837 A | 6/1998 |

(Continued)

OTHER PUBLICATIONS

Orchard, N. et al., "The Design, Calibration and Use of an Ultrasonic Probe on a CMM," Rolls-Royce Plc, Derby, UK (2006).
(Continued)

*Primary Examiner* — Yi-Shan Yang
(74) *Attorney, Agent, or Firm* — Oliff PLC

(57) ABSTRACT

An ultrasound probe is described that comprises a transducer for transmitting and receiving ultrasound. The probe also includes a coupling element, such as a spherical ball of self-lubricating or hydrogel material, for contacting and acoustically coupling to an object to be inspected. The ultrasound probe also includes an analyser that is arranged to analyse the ultrasound signal received by the transducer and thereby determine if there is contact between the coupling element, and the surface of an object. The probe can thus be used for internal (ultrasound) inspection of objects as well as measuring the position of points on the surface of the object. The probe may be mountable to a coordinate measuring machine or other moveable platforms.

18 Claims, 15 Drawing Sheets

Figure 1A:
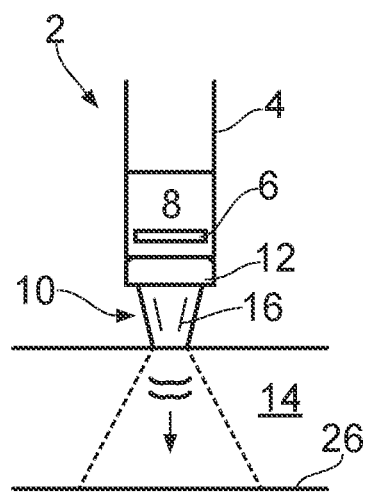

(51) Int. Cl.
  *G01N 29/28* (2006.01)
  *G01N 29/11* (2006.01)
  *G01B 17/02* (2006.01)
  *G01B 21/04* (2006.01)
  *A61B 8/00* (2006.01)
  *A61B 8/08* (2006.01)

(52) U.S. Cl.
  CPC .............. *G01B 17/02* (2013.01); *G01B 21/04* (2013.01); *G01N 29/11* (2013.01); *G01N 29/28* (2013.01); *A61B 8/483* (2013.01); *G01N 2291/011* (2013.01); *G01N 2291/012* (2013.01); *G01N 2291/02854* (2013.01); *G01N 2291/044* (2013.01); *G01N 2291/101* (2013.01)

(56) References Cited

U.S. PATENT DOCUMENTS

| | | | |
|---|---|---|---|
| 4,459,854 | A | 7/1984 | Richardson et al. |
| 4,584,879 | A | 4/1986 | Webster et al. |
| 4,785,545 | A | 11/1988 | Aubele |
| 4,905,700 | A | 3/1990 | Wokalek et al. |
| 5,189,806 | A | 3/1993 | McMurtry et al. |
| 5,718,228 | A | 2/1998 | Hiruta et al. |
| 5,728,937 | A | 3/1998 | Reichau et al. |
| 6,039,694 | A * | 3/2000 | Larson ................ A61B 8/4281 73/644 |
| 6,092,420 | A | 7/2000 | Kimura et al. |
| 6,131,459 | A | 10/2000 | Seale et al. |
| 6,343,512 | B1 | 2/2002 | Bourne et al. |
| 8,002,704 | B2 | 8/2011 | Torp et al. |
| 8,931,343 | B2 | 1/2015 | Bond-Thorley |
| 2005/0016298 | A1 | 1/2005 | Hill |
| 2005/0085725 | A1* | 4/2005 | Nagar ................ G01S 15/8968 600/437 |
| 2005/0166413 | A1 | 8/2005 | Crampton |
| 2006/0109002 | A1 | 5/2006 | Buschke et al. |
| 2007/0039371 | A1 | 2/2007 | Omata et al. |
| 2007/0144263 | A1 | 6/2007 | Fei et al. |
| 2007/0181139 | A1 | 8/2007 | Hauck |
| 2008/0021317 | A1 | 1/2008 | Sumanaweera |
| 2008/0235970 | A1 | 10/2008 | Crampton |
| 2009/0165317 | A1 | 7/2009 | Little |
| 2009/0178482 | A1 | 7/2009 | Hough et al. |
| 2010/0174189 | A1 | 7/2010 | Abraham |
| 2010/0280371 | A1 | 11/2010 | Lacoste |
| 2011/0112397 | A1 | 5/2011 | Shen et al. |
| 2012/0250465 | A1 | 10/2012 | Seuthe |
| 2013/0047452 | A1* | 2/2013 | McMurtry ............ G01B 5/012 33/503 |
| 2013/0145848 | A1 | 6/2013 | Jun et al. |
| 2013/0195573 | A1 | 8/2013 | Podiebrad |
| 2014/0005556 | A1 | 1/2014 | Hirota et al. |
| 2014/0051969 | A1 | 2/2014 | Suzuki |
| 2014/0260627 | A1* | 9/2014 | Ferrari ................ G01B 21/04 73/618 |
| 2015/0022505 | A1 | 1/2015 | Lee |
| 2015/0177194 | A1 | 6/2015 | Xu et al. |
| 2015/0272544 | A1 | 10/2015 | Raum et al. |
| 2016/0074017 | A1* | 3/2016 | Lee .................... G01S 7/52046 600/443 |
| 2016/0075612 | A1* | 3/2016 | Lopez Villanueva . C09K 17/22 523/132 |
| 2017/0276651 | A1 | 9/2017 | Hall |

FOREIGN PATENT DOCUMENTS

| | | |
|---|---|---|
| CN | 1469720 A | 1/2004 |
| CN | 201497494 U | 6/2010 |
| CN | 101984919 A | 3/2011 |
| CN | 102105784 A | 6/2011 |
| DE | 19748317 C1 | 6/1999 |
| EP | 0420758 A1 | 4/1991 |
| EP | 0527651 A1 | 2/1993 |
| EP | 2003-000592 A | 1/2003 |
| EP | 1926969 B1 | 8/2009 |
| EP | 2487455 A1 | 8/2012 |
| GB | 2440959 B | 2/2008 |
| GB | 2461864 A | 1/2010 |
| GB | 2463293 A | 3/2010 |
| JP | S60-225544 A | 11/1985 |
| JP | S62-176260 U | 11/1987 |
| JP | S62276456 A | 12/1987 |
| JP | H02-243137 A | 9/1990 |
| JP | H05-30909 A | 2/1993 |
| JP | H5-309092 A | 11/1993 |
| JP | H06-46495 A | 2/1994 |
| JP | H07-239217 A | 9/1995 |
| JP | H07-327994 A | 12/1995 |
| JP | 2000-111330 A | 4/2000 |
| JP | 2003-000592 A | 1/2003 |
| JP | 2004-198307 A | 7/2004 |
| JP | 2004-264275 A | 9/2004 |
| JP | 2007-527323 A | 9/2007 |
| JP | 2009-507239 A | 2/2009 |
| WO | 85/00651 A1 | 2/1985 |
| WO | 94/22373 A1 | 10/1994 |
| WO | 97/35164 A1 | 9/1997 |
| WO | 02/016965 A3 | 2/2003 |
| WO | 2004/096502 A1 | 11/2004 |
| WO | 2005/015121 A1 | 2/2005 |
| WO | 2005-057205 A1 | 6/2005 |
| WO | 2007/028941 A1 | 3/2007 |
| WO | 2008/012535 A2 | 1/2008 |
| WO | 2009/024783 A1 | 2/2009 |
| WO | 2009/085558 A1 | 7/2009 |
| WO | 2014/005530 A1 | 1/2014 |

OTHER PUBLICATIONS

Wikipedia, "Superabsorbent Polymer.", http://en.wikipedia.org/wiki/Superabsorbent_polymer, pp. 1-5, (2014).
U.S. Appl. No. 15/510,761, filed Mar. 13, 2017 in the name of Liam Hall.
U.S. Appl. No. 15/510,791, filed Mar. 13, 2017 in the name of Liam Hall.
Sep. 4, 2018 Office Action issued in U.S. Appl. No. 15/510,761.
Aug. 21, 2018 Office Action issued in Chinese Patent Application No. 201580052932.3.
Oct. 8, 2018 Office Action issued in Chinese Patent Application No. 201580053123.4.
Shen, Yudi "Modern Nondestructive Testing Technology" Xi'an Jiaotong University Postgraduate Innovation Education Material, Xi'an Jiaotong University Press, pp. 67-77, Aug. 9, 2018.
Jan. 28, 2019 Office Action issued in U.S. Appl. No. 15/510,761.

* cited by examiner

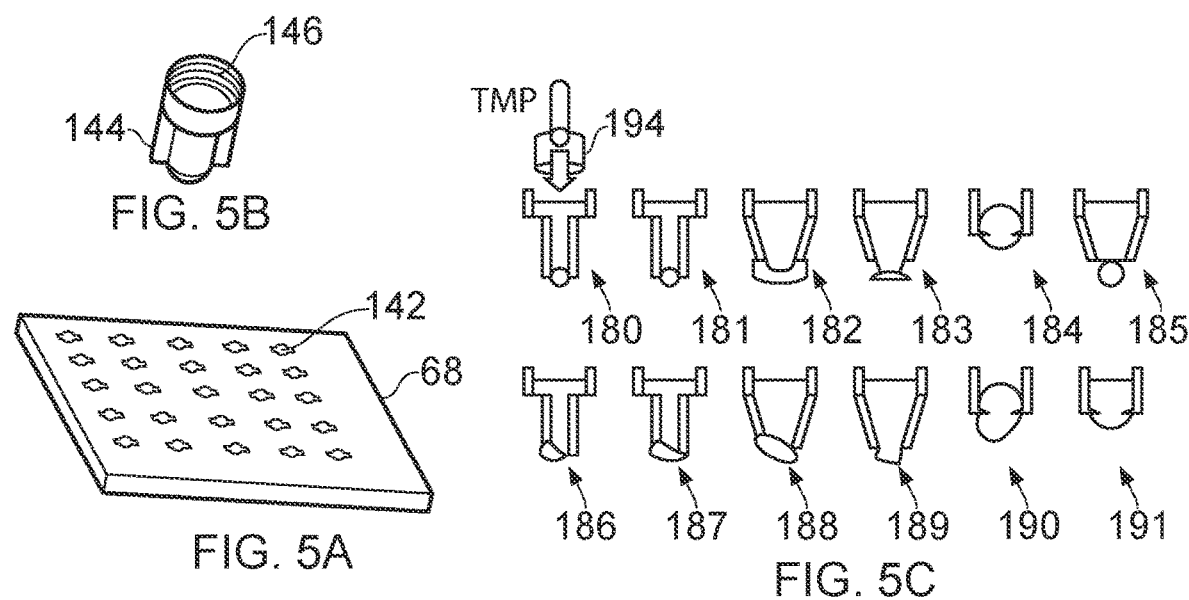
FIG. 5B
FIG. 5A
FIG. 5C
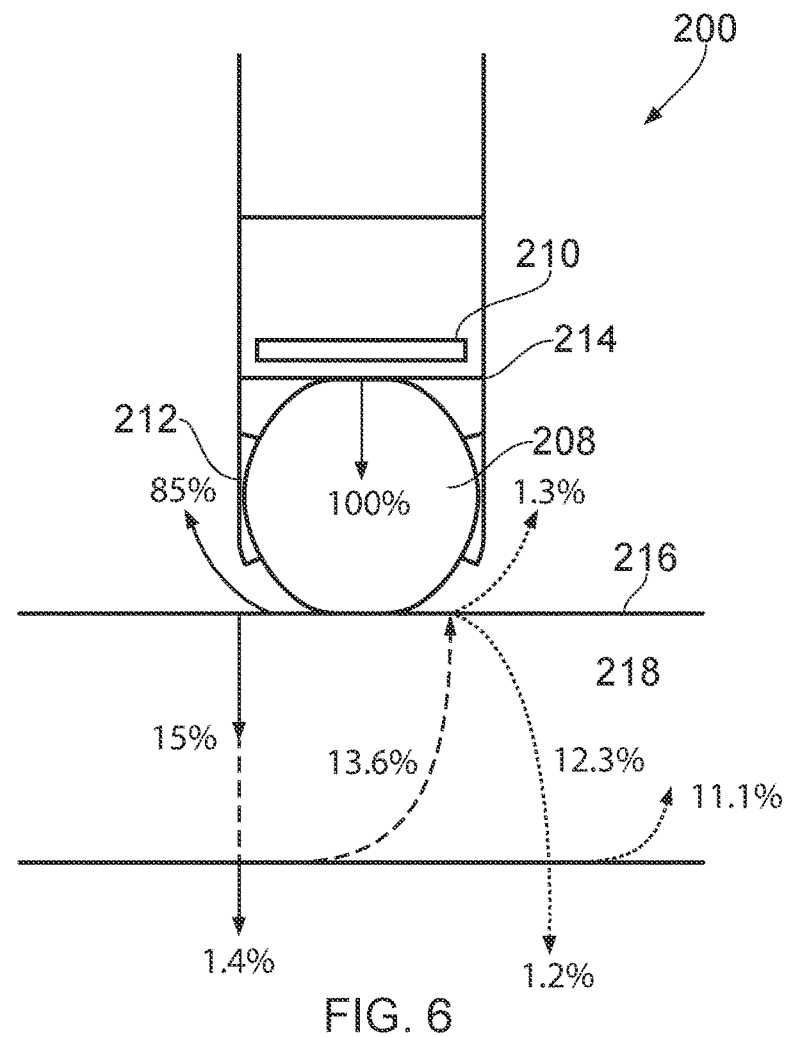
FIG. 6

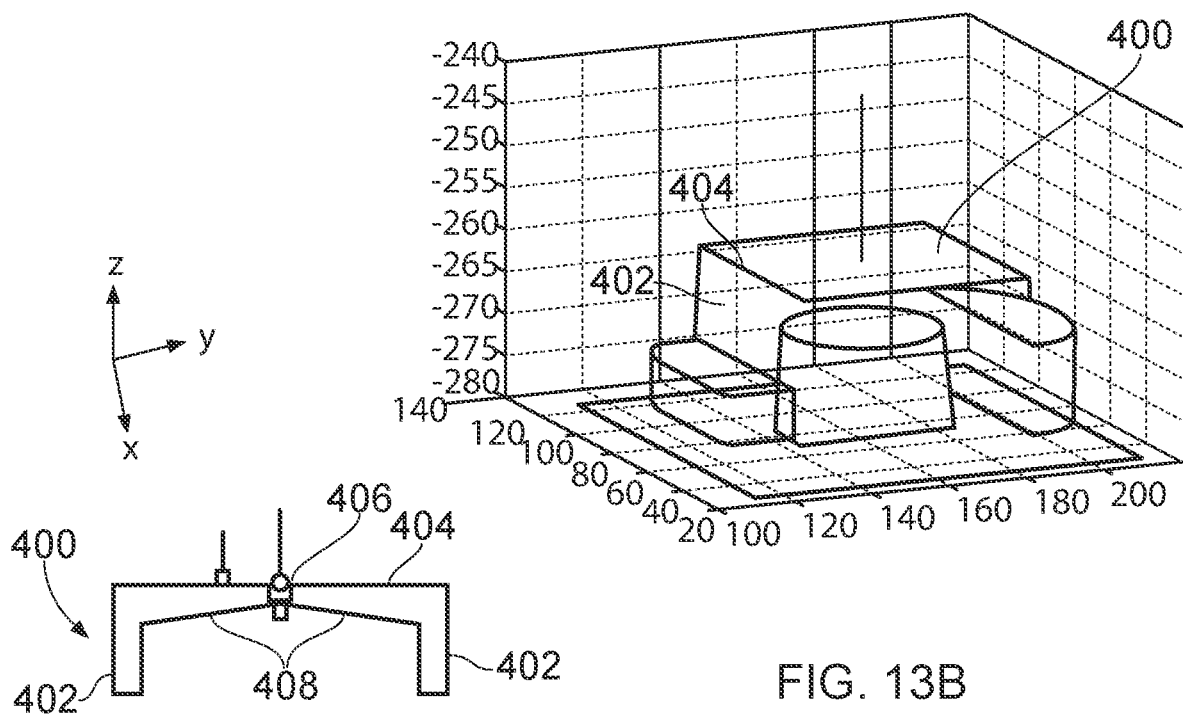
FIG. 13A
FIG. 13B
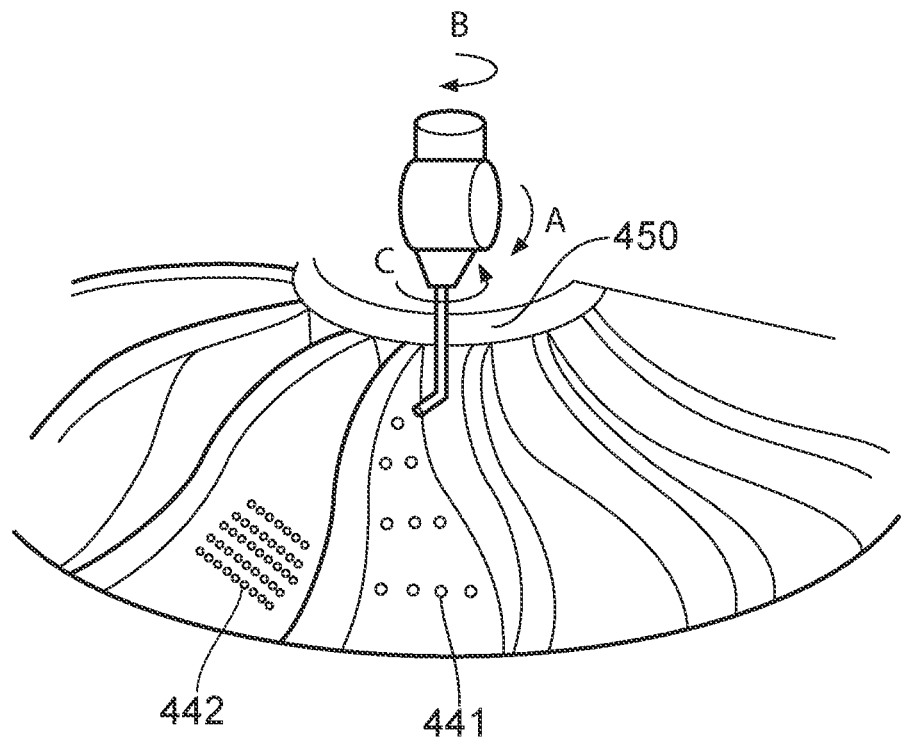
FIG. 14

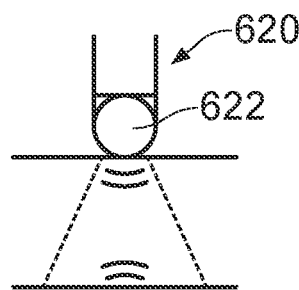
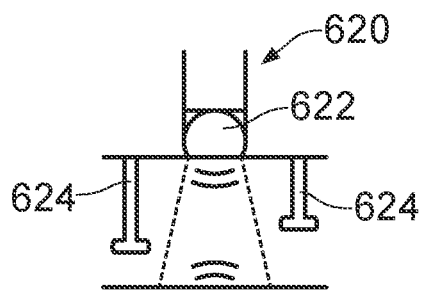
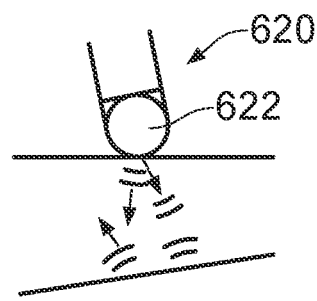
FIG. 22A     FIG. 22B     FIG. 22C
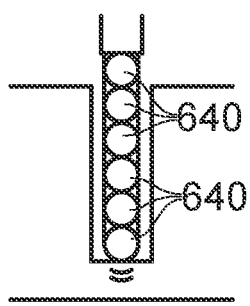
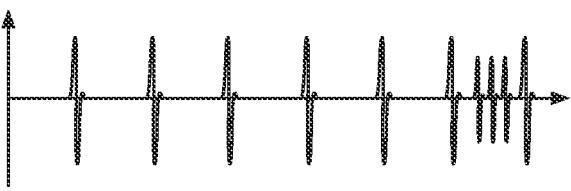
FIG. 23
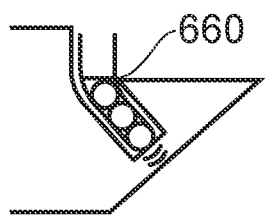
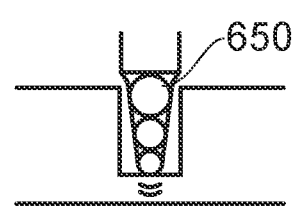
FIG. 24
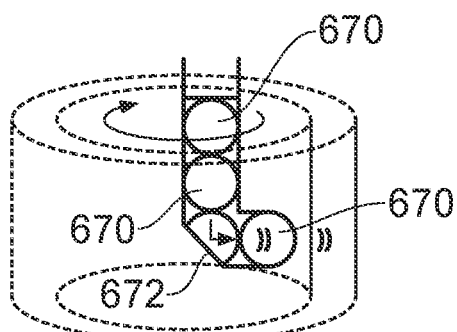
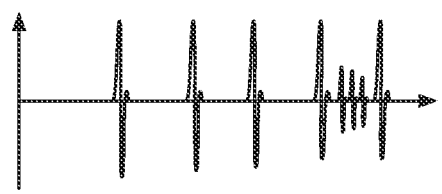
FIG. 25

MEASUREMENT PROBE

This application is a Continuation of application Ser. No. 15/510,791, filed Mar. 13, 2017, which is a national stage of PCT/GB2015/052814, filed Sep. 29, 2015, which claims priority to GB 1417164.9, filed Sep. 29, 2014. The entire contents of the prior applications are hereby incorporated by reference herein in their entirety.

The present invention relates to ultrasound inspection apparatus and in particular to an ultrasound probe that can acquire both ultrasound and surface contact measurements of an object.

It is known to measure the dimensions of manufactured objects to ensure they conform to tolerance. In the case of high value components, such as aerospace turbine blades, the external form of an object can be measured to sub-micron accuracy using a surface contact probe mounted on a CMM. Examples of techniques for measuring the positions of multiple points on the surface of an object using a CMM equipped with a surface contact (e.g. scanning) probe are described in U.S. Pat. No. 5,189,806 and WO2009/024783.

In addition to surface measurements, it is often necessary to measure the internal features of an object. For example, turbine blades are typically hollow to enable them to be both light-weight and strong for operation at extreme temperatures and pressures. The internal inspection of such hollow turbine blades is typically carried out using ultrasound inspection. Ultrasound thickness gauging probes, which typically rely on the localised application of a couplant material (e.g. a coupling gel or liquid) to the part, are known. Such probes tend to be handheld and provide thickness measurements when placed into contact with a point on the surface of the object being inspected. It has been described previously how an ultrasound probe may be mounted to the quill of a CMM. For example, US2009/0178482 describes an ultrasound probe mounted to the quill of a CMM. US2009/0178482 also describes how the CMM may interchangeably use the ultrasound probe and a standard surface contact probe for internal and external (surface position) measurements respectively.

According to a first aspect of the present invention, there is provided an ultrasound probe comprising;
  a transducer for transmitting and receiving ultrasound, and
  a coupling element for contacting and acoustically coupling to an object to be inspected,
  wherein the ultrasound probe comprises an analyser arranged to analyse the ultrasound signal received by the transducer and thereby determine if there is contact between the coupling element and the surface of an object.

The present invention thus relates to an ultrasound probe that includes a transducer for transmitting and receiving ultrasound. The ultrasound transducer may, for example, comprise a pulse-echo ultrasonic transducer that includes a piezo-electric element for transmitting high frequency time-discrete longitudinal waveforms (hereinafter termed "L-waves"). The ultrasound probe also includes a coupling element (e.g. a hydrophilic sphere or other tip as described below) that is designed to contact and acoustically couple with the object to be inspected. An analyser is also provided to analyse the ultrasound signal received by the transducer (e.g. the echoes returned following an excitation pulse) and use that received signed to establish if there is contact between the coupling element and the surface of an object. The ultrasound probe of the present invention is particularly advantageous when mounted to coordinate positioning apparatus because it permits the position of points on the surface of an object to be measured.

The present invention thus provides an ultrasound probe that not only allows the internal features (e.g. thickness) of objects to be measured but also determines when the probe contacts an object or is moved out of contact with an object. This allows the probe to be used for both thickness and surface position measurements. In other words, the ultrasound probe of the present invention removes the need to use a separate surface contact (e.g. touch trigger) measurement probe in combination with an ultrasound probe. The ultrasound probe of the present invention can perform both internal and external tasks, thereby increasing the speed of part inspection.

The transducer may be configured to operate in any suitable mode. The ultrasound probe may operate at a high frequency. For example, the operating frequency may be greater than 5 MHz, greater than 10 MHz or more preferably greater than 15 MHZ. In a preferred embodiment, the operating frequency is around 20 MHz. The transducer, which may comprise a piezoelectric element, preferably excites longitudinal sounds waves (L-waves). Advantageously, the transducer is arranged to periodically transmit an excitation pulse and subsequently receive the returned ultrasound signal (i.e. pulse-echo mode operation). The amplitude of the ultrasound signal received after each excitation pulse may then be measured as a function of time to provide an amplitude scan (also termed an A-scan). A plurality of such scans may be combined and averaged, if required. The analyser may determine if there is contact between the coupling element and an object from differences in successive A-scans.

Advantageously, each amplitude scan includes amplitude peaks relating to internal reflections of ultrasound from within the probe. The internal reflections may arise from a delay line, the coupling element or other interfaces between different type of material within the probe. The analyser may determine if there is contact between the coupling element and an object from changes in the amplitudes of the internal reflections between successive amplitude scans. Alternatively, the analyser may determine if there is contact between the coupling element and the object by assessing if internal reflections from a contacted object are present in each amplitude scan. For example, the appearance of additional reflection peaks may be used to indicate the existence of back wall reflections from an object and hence that contact with an object has been established. In addition to determining if contact with an object has been established, it is also possible to determine when contact with an object has been lost in a similar manner.

Conveniently, the ultrasound probe outputs a trigger signal that indicates when the analyser has determined the coupling element is in contact with an object. In other words, the ultrasound probe may issue a trigger signal when an object is contacted. For example, a trigger signal output line may be held high (status "1") to indicate when there is contact with an object and held low (status "0") to indicate no object contact. The transition from low to high thus indicates contact has been made, and high to low indicates contact has been lost. Such a trigger signal may be fed to the controller of a coordinate positioning apparatus and used to determine the position of points on the surface of an object in a similar manner to measurements taken with a traditional touch trigger probe.

In addition to determining when contact with an object is lost or established, the ultrasound probe may also determine when optimum acoustic coupling with an object is obtained.

In particular, the analyser may assess when the "coupling sweet spot" is attained by monitoring reflections from the object as the probe is pressed into the object with increasing or decreasing force. In particular, the analyser preferably determines when optimum ultrasound coupling with an object is achieved by monitoring internal ultrasound reflections from the contacted object as the coupling element is moved into closer engagement with the object. Once the "coupling sweet spot" is attained, ultrasound measurements (e.g. thickness measurements, crack detections measurements etc) may then be acquired.

The ultrasound probe can also probe the internal structure of the object using the ultrasound that is coupled into the object. Advantageously, the analyser determines the thickness of a contacted object from internal ultrasound reflections from the contacted object. Preferably, the analyser assesses the thickness of a contacted object from successive reflections from the back wall of the object. In other words, the probe may measure thickness using the so-called Mode-3 operation that is described in more detail below. It would, of course, be possible to use different modes of operation (e.g. Mode-1 or Mode 2) for the ultrasound inspection. The probe may thus be configured to operate in any one of a plurality of different ultrasound measurement modes. The thickness measurements may require a calibration step to be performed (e.g. to measure the speed of sound in the material of the part being inspected). The ultrasound probe may comprise a probe housing in which the transducer and coupling element are provided. The analyser may be provided within the probe housing or in an interface external to the probe housing.

Advantageously, the coupling element comprises an elastically deformable material. If internal reflections from the coupling element are being monitored, deformations of the coupling element alter such reflections. Elastic deformability also means the coupling element returns to the same shape after a distorting force is removed. Such elasticity is thus beneficial as it allows repeatable and accurate touch contact measurements to be made. It is also preferable for the coupling element to be substantially spherical as surface contact measurements are then highly repeatable.

The coupling element of the probe may comprise a dry couplant material, such as silicone rubber or the like. The coupling element may require the application of a coupling material (e.g. water or gel) to ensure good acoustic coupling. The coupling element could comprise a compressible and easily pliable oil-based thermo-softening plastic with low acoustic attenuation properties.

Advantageously, the coupling element comprises a self-lubricating material. Such a self-lubricating material preferably releases a lubricant, such as water and/or oil, from its external surface in a controlled manner. The self-lubricating material may comprise an oleophilic elastomer. Advantageously, the self-lubricating material comprises a hydrophilic elastomer. For example, the hydrophilic elastomer may comprise a incompressible gelatinous hydrophilic elastomer material such as a lightly cross-linked hydrophilic vinyl elastomer or a super absorbent polymer hydrogel. An example of a high water content hydrophilic polymer chain compounds is MMA:VP (i.e. a Copolymer of N-vinyl pyrolidone and methyl methacylate). For this compound, the water content can vary from about 35% to 95% and excellent acoustic properties are exhibited although the tear strength decreases as the water content is increased. Conveniently, the self-lubricating material is provided as a sphere. A preferred embodiment thus comprises a coupling element comprising a hydrophilic elastomer sphere.

The provision of a coupling element comprising a hydrophilic elastomer sphere has a number of advantages. For example, water swelling hydrophilic polymer spheres release a limited amount of water from their surface (i.e. they "sweat" water). This released water provides improved acoustic coupling with an object by filling any pockets of air between the ultrasound probe and a rough surface of that object. The amount of water released from the hydrophilic elastomer sphere can be controlled by appropriate selection of the chemical properties of the polymer material. For example, the amount of released water can be arranged to be minimal and will thus evaporate quite readily in the atmosphere without leaving any residual contaminant. Furthermore, such hydrophilic elastomer spheres can be soft and elastic to provide a high degree of conformity against a curved inspection surface. The release of the water can also act as a lubricant that permits such spheres to be scanned along a path on the surface of an object. Furthermore, hydrophilic materials have inherently low acoustic attenuation and an acoustic impedance value that is well suited to ultrasonic transmission between a ceramic transducer wear plate and metallic part.

Advantageously, the ultrasound probe comprises a delay line. The probe may include a coupling element that also acts as a delay line. For example, a coupling element may be provided that comprises a hydrophilic elastomer sphere that has a protruding portion for contacting the object to be inspected and is sufficiently large to provide a delay line function. Conveniently, the probe comprises a delay line that is coupled to the coupling element. In other words, a delay line (e.g. a solid plastic delay line) that is separate to the coupling element may be provided. Such a delay line may, for example, be formed from Polystyrene or Polycarbonate. A hydrophilic elastomer sphere may be coupled to the distal end of the delay line. The delay line may thus be placed in the acoustic path between the transducer and the coupling element.

Advantageously, the ultrasound probe comprises an ultrasound beam control element. The ultrasound beam control element preferably manipulates (e.g. refracts, steers or focuses) the ultrasonic wavefront that is transmitted into, and/or is received from, the object being inspected. Preferably, a delay line is provided that also acts as the ultrasound beam control element. For example, the ultrasound probe may comprise a tapered delay line that results in a more divergent far-field beam. An ultrasound beam control element may also be provided in the form of an acoustic lens. For example, a spherically focused planar concave lens could be provided. A hydrophilic elastomer sphere could then be coupled to the concave lens (e.g. so the lens cups around the sphere) to provide refractive focusing to increase back wall reflections. An ultrasound beam control element may be provided in the form of a refractive wedge. For example, an asymmetric rigid wedge could be provided that refracts the projected ultrasonic beam into the inspection surface at some set angle from the normal direction as determined by the relative speed of sound in the coupled material. This can be useful for internal metrology measurements of more complex geometries where the front wall and back wall are not parallel. Acoustic mirrors and other acoustic components may be included in the probe, as required.

Advantageously, the ultrasound probe comprises an ultrasound absorbing shell. The ultrasound absorbing shell suppresses or attenuates all unwanted acoustic reflections from within the shell walls that may otherwise interfere with the reflected waveform of interest. The ultrasound absorbing shell may be formed from, for example, Teflon® or glass-filled PTFE.

The ultrasound probe may be provided as unitary item. Advantageously, the ultrasound probe is a modular probe. The probe thus preferably comprises a base module that comprises the transducer and a coupling module that comprises the coupling element. The base module may comprise a first connector portion and the coupling module a second connector portion. The first connector portion is preferably releasably attachable to the second connector portion. The base module of the probe may be attached, or attachable, to the moveable member of a coordinate positioning apparatus. For example, the base module may include an attachment feature or mechanism that permits it to be attached to the quill, or rotary head, of a CMM.

The ultrasound probe may thus form part of modular ultrasound inspection apparatus that includes a base module and a plurality of coupling modules. This allows different coupling modules to be attached to the base module as and when required. The attachment and detachment of coupling modules is preferably performed in an automated manner by appropriate programming of the coordinate positioning apparatus. The plurality of coupling modules may include a range of different coupling modules (e.g. that direct sound in different directions and/or with different amounts of divergence) for measuring different internal features of a part. The plurality of coupling modules may alternatively or additionally include a range of similar coupling modules that have a limited lifetime (e.g. due to wear or damage of a soft coupling element) and can thus be replaced when damaged, worn or after being used for a certain period of time. The plurality of coupling modules may thus be consumable items that have a short lifetime compared with the base module.

Advantageously, a holder (e.g. a storage tray) is provided for retaining the plurality of coupling modules. The holder may be attachable to the bed of coordinate positioning apparatus. For example, the holder may include one or more features (e.g. screws holes, magnets etc) that allow the holder to be secured to the bed of a CMM in a fixed position and orientation. The holder may include one or more ports or receptacles, each port or receptacle arranged to retain a coupling module. The holder can thus store the coupling modules that are not presently being used; i.e. coupling modules that are not attached to the base module for measurement purposes can be stored in the holder. The holder may store more than five, more than ten or more than fifteen coupling modules. The apparatus may thus comprise more than five, more than ten or more than fifteen coupling modules. The plurality of coupling modules may comprise a plurality of different designs or types of coupling modules. The plurality of coupling modules may comprise a plurality of substantially identical coupling modules.

As explained above, contact modules can be provided in which the coupling element is self-lubricating (e.g. slowly releases water). The holder may thus be hermetically sealed prior to use. This prevents the coupling elements (e.g. hydrophilic spheres) from drying out prior to use. The holder may be re-sealable. For example, the holder may be opened and closed after each coupling module is taken or it may be opened and then closed after a set of measurements have been acquired. Alternatively, the holder (and optionally the coupling modules having self-lubricating coupling elements) may be provided as a single-use or consumable item that is opened, used and then discarded or recycled. The holder may initially contain coupling modules comprising de-hydrated hydrophilic spheres that are hydrated prior to use. A new holder may thus be opened as and when required.

In a preferred embodiment, the holder comprises a plurality of recesses for receiving the plurality of coupling modules. Conveniently, the recesses and coupling modules are arranged to prevent rotation of a coupling module when located in a recess. For example, the coupling modules may include a central hub with one or more radially protruding wings. The holder may then comprise a complimentary recess. A coupling module may thus be placed into and withdrawn from a recess using vertical (linear) relative motion. Once inserted, rotation of the coupling module relative to the holder is prevented.

The first and second connector portions may be provide by any mechanical linkage. For example, a magnetic connection arrangement may be provided. Advantageously, the first and second connector portions comprise complementary screw threads. For example, the first connector portion of the base module may comprise a screw thread provided on the outer surface of the distal end of the base module housing (e.g. a male screw-thread connector). The second connector portions of the coupling modules may then include a recess with an internally screw threaded surface (e.g. a female screw-thread connector). The arrangement may be such that the base module and coupling module can engage and disengage from each other by imparting relative rotary motion. This allows a base module (e.g. held by a rotary head) to be screwed into and out of engagement with a coupling module. The coupling modules may conveniently be stored in a holder of the type described above that prevent rotation during the attachment process.

Attachment of one of the plurality of coupling modules to the base module preferably establishes a reliable and repeatable acoustic linkage between the modules. In particular, mating the first and second connector portions provides an acoustic link between the transducer of the base module and the coupling element of the coupling module. The base module thus preferably comprises a transducer having a wear plate. The wear plate is conveniently arranged to acoustically couple with a coupling module attached to the base module. For example, the wear plate may engage the delay line of a coupling module or it may directly engage a hydrophilic elastomer sphere of a coupling module. In such an embodiment, attachment of one of the plurality of coupling modules to the base module holds the relevant part of the coupling module (e.g. delay line, sphere etc) firmly against the transducer wear plate.

The present invention also extends to a coordinate positioning apparatus that includes the above described ultrasound probe. The ultrasound probe may be mountable, or mounted, to the moveable member of the coordinate positioning apparatus. The coordinate positioning apparatus may include a machine tool, an industrial robot, an arm, an x-y scanner or a crawler. In a preferred embodiment, the coordinate positioning apparatus comprises a coordinate measuring machine. The CMM may be a Cartesian (e.g. bridge type) of CMM or a non-Cartesian (e.g. hexapod) type of CMM. The CMM preferably comprises a rotary head that provides the moveable member to which the probe is attached. The rotary head may comprise a single rotary axis, two rotary axes or three rotary axes. The rotary head advantageously comprises at least two rotary axes. The rotary head may comprise at least three rotary axes.

According to a further aspect of the invention, there is described a method of operating a pulse-echo ultrasound probe mounted to coordinate positioning apparatus to acquire surface position measurements. The method comprises the step of monitoring the echoes of received ultrasound signals for changes indicative of contact with an object. An ultrasound probe may thus be adapted to also acquire surface contact measurements.

According to a further aspect of the invention, an ultrasound inspection device for coordinate positioning apparatus is provided. The device comprises an ultrasound transducer and a coupling element for contacting and acoustically coupling to an object to be inspected, wherein the coupling element comprises self-lubricating material. The speed of sound within the coupling element may be measured by analysis of reflections from within the coupling element when the coupling element is subject to a plurality of different deformations. The ultrasound inspection device may be a modular design, as described above, or a single (unitary or non-modular) arrangement. The device may comprise any of the features mentioned herein. Advantageously, the self-lubricating material comprises a hydrophilic elastomer. Conveniently, the self-lubricating material comprises a super absorbent polymer hydrogel. Preferably, the coupling element comprises a sphere of self-lubricating material. The ultrasound inspection device may be used in a method of measuring the porosity and/or density of a part, such as a part made using an additive manufacturing technique.

The present invention also extends to a method of measuring the thickness of an object, and/or points on the surface of an object, using apparatus described above.

Figure 1B:
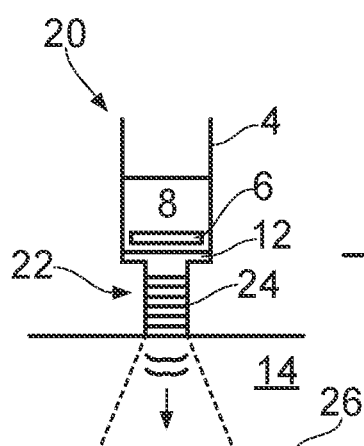
Figure 1C:
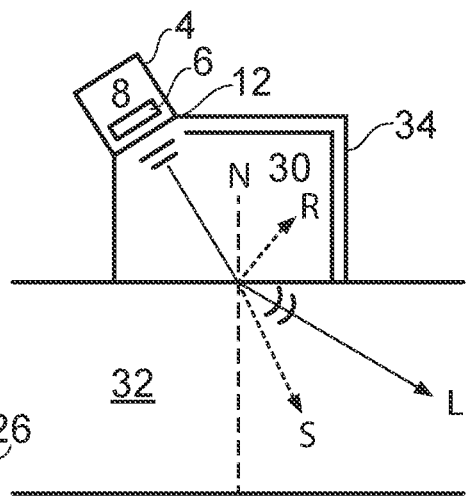
Figure 2A:
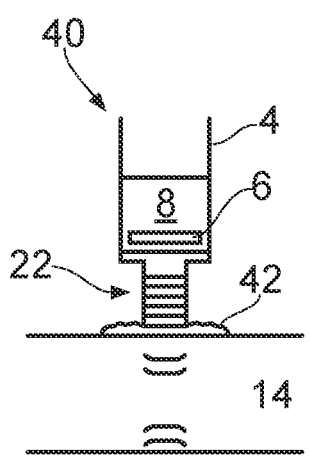
Figure 2B:
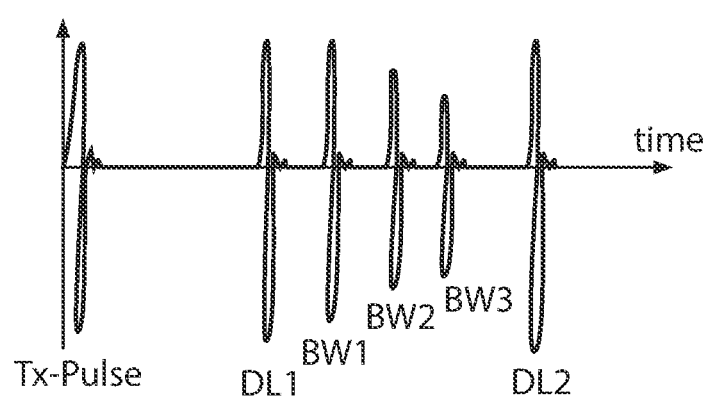
Figure 3:
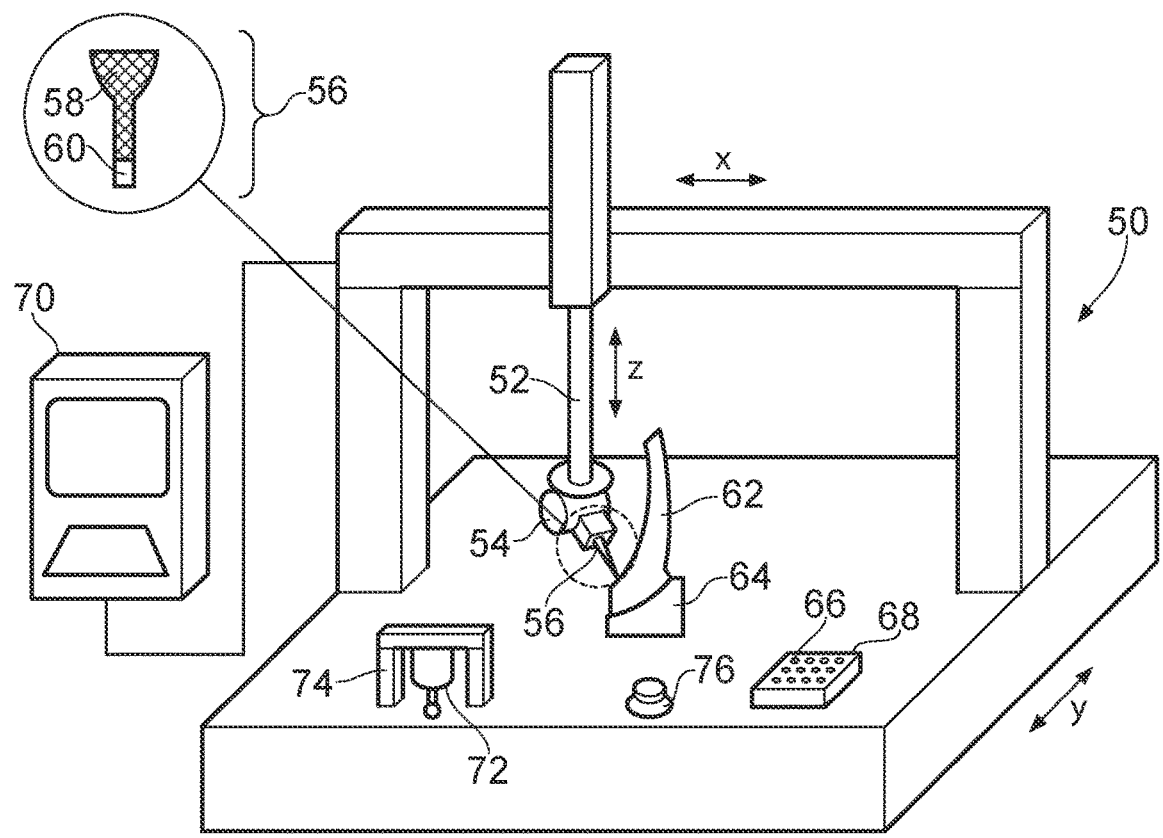
Figure 7:
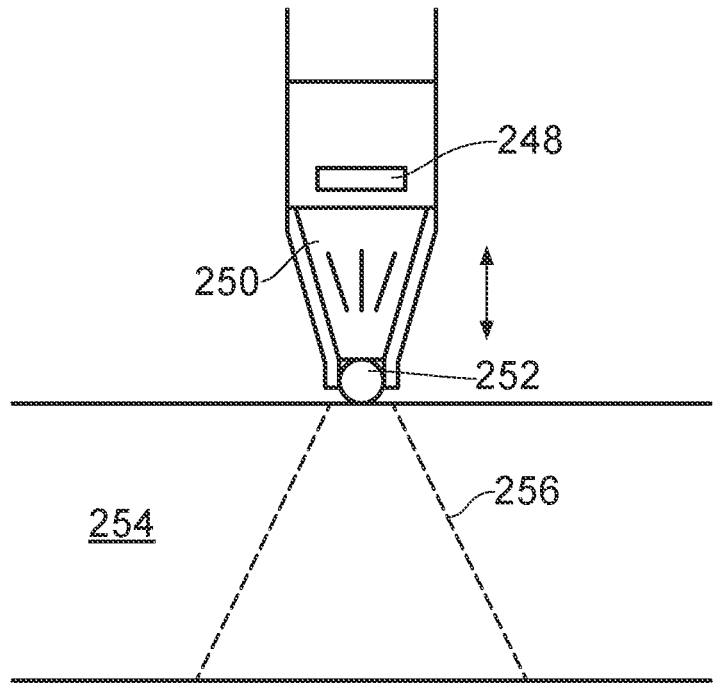
Figure 8:
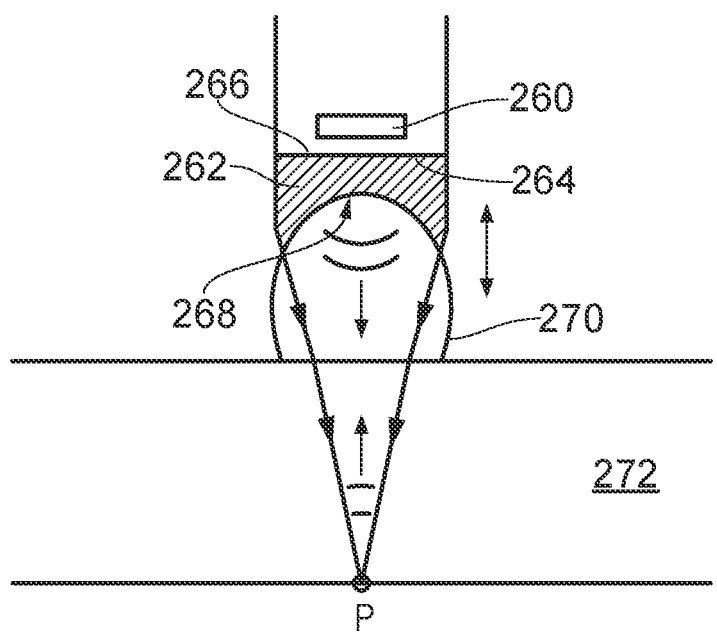
Figures 9A, 9B, 9C:
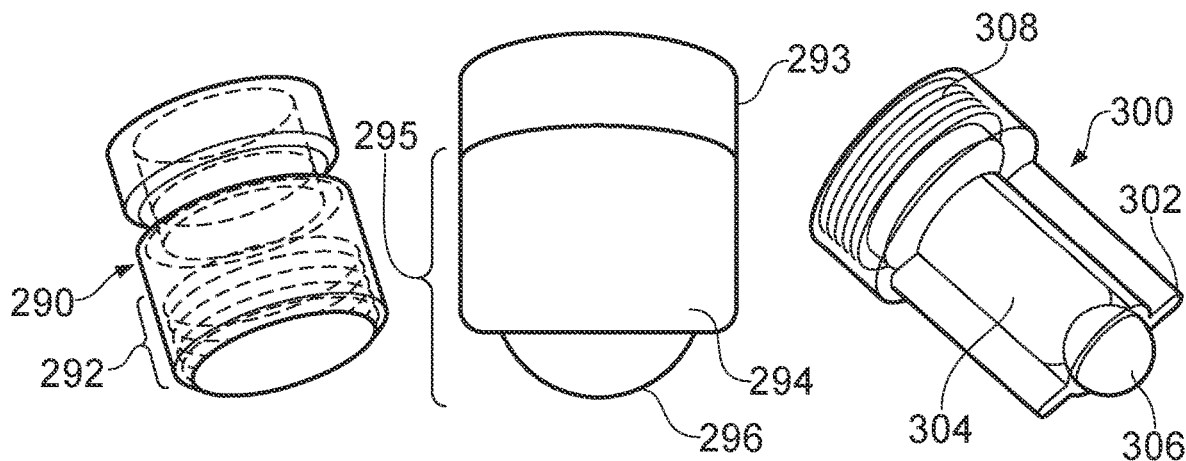
Figures 10A, 10B:
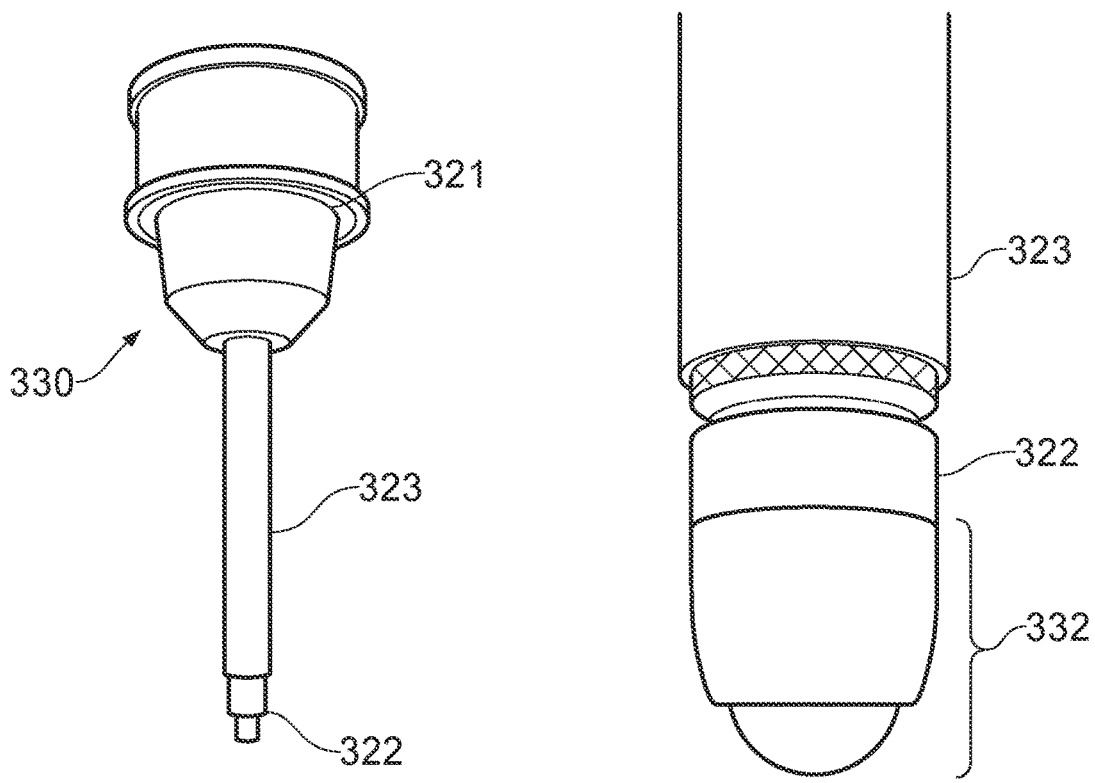
Figure 11:
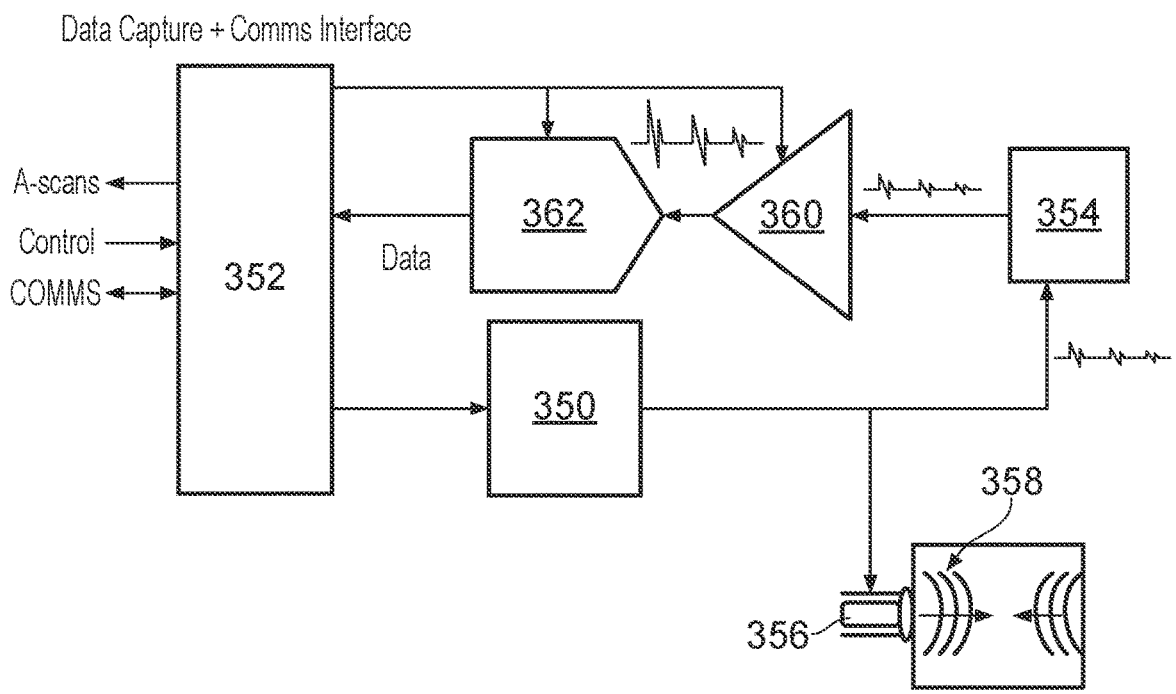
Figure 12:
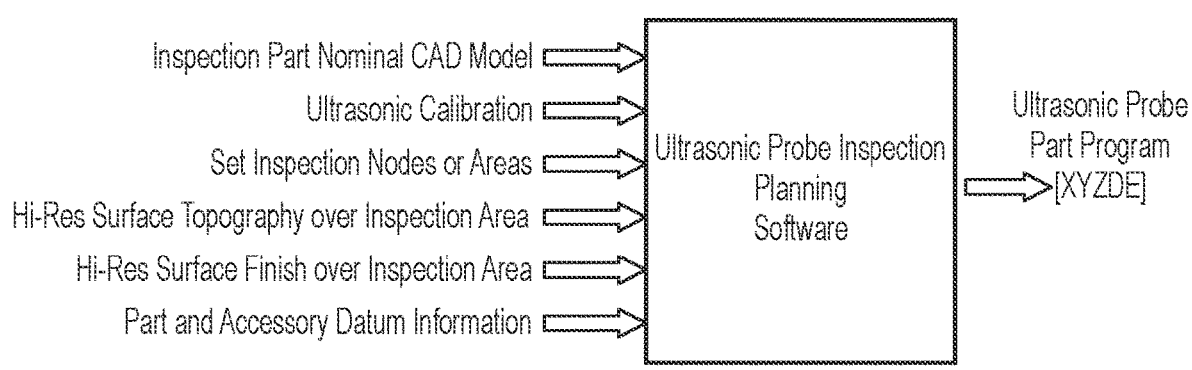
Figure 15A:
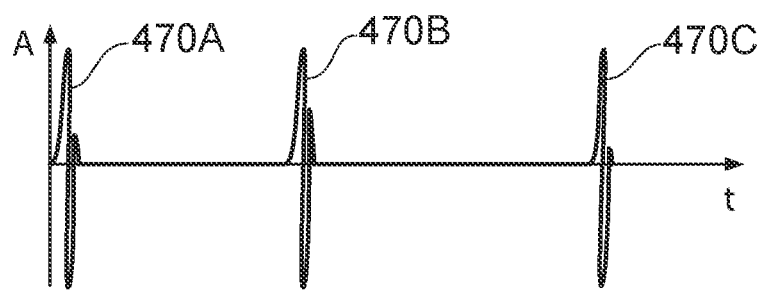
Figure 15A:
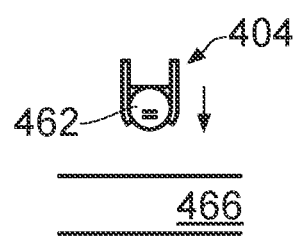
Figure 15B:
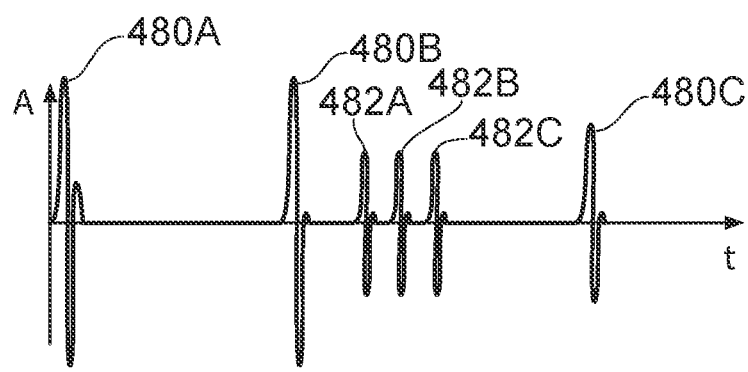
Figure 15B:
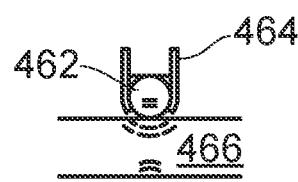
Figure 15C:
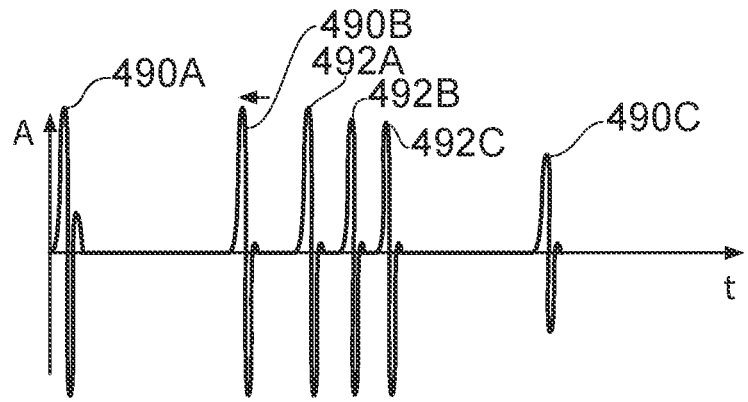
Figure 15C:
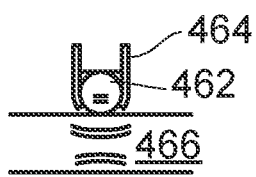
Figure 15D:
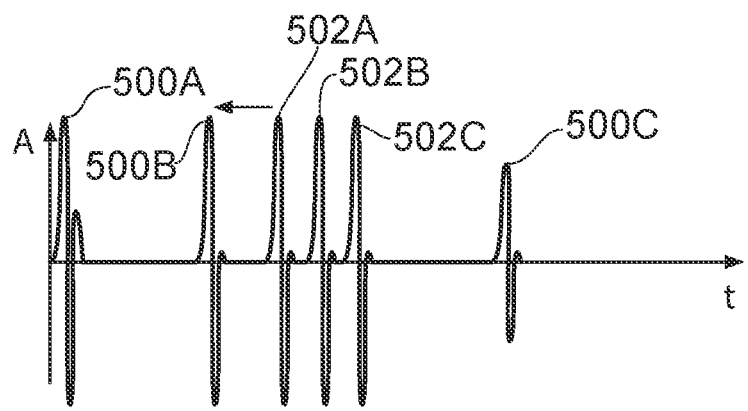
Figure 15D:
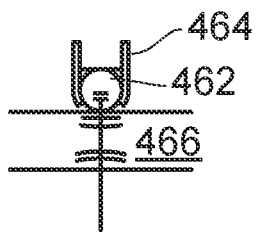
Figure 16:
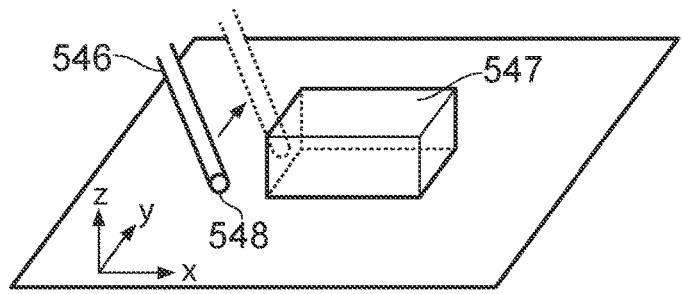
Figures 17A, 17B:
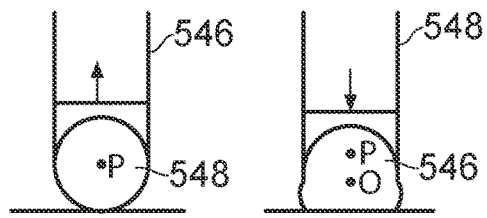
Figure 18:
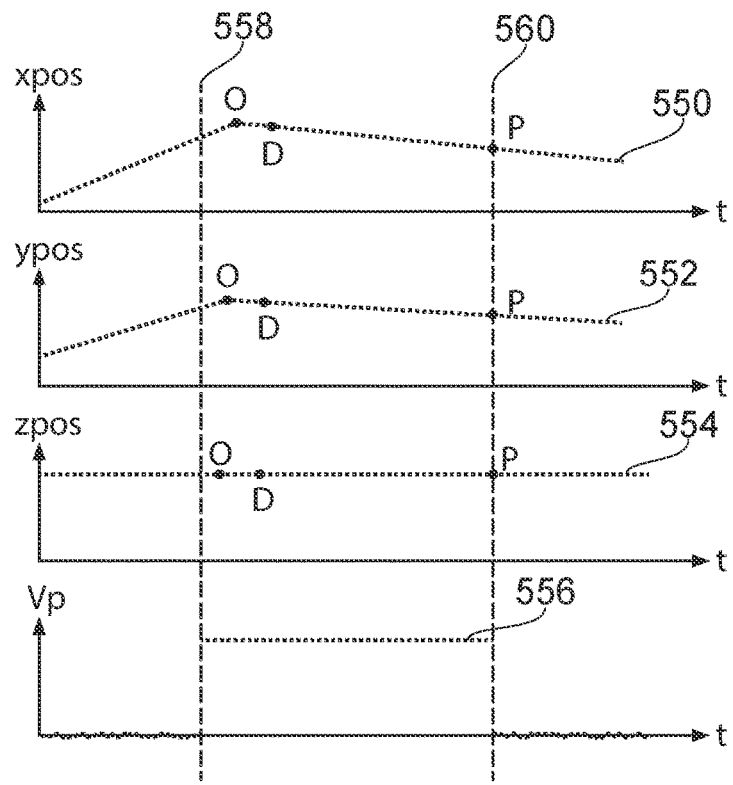
Figure 19:
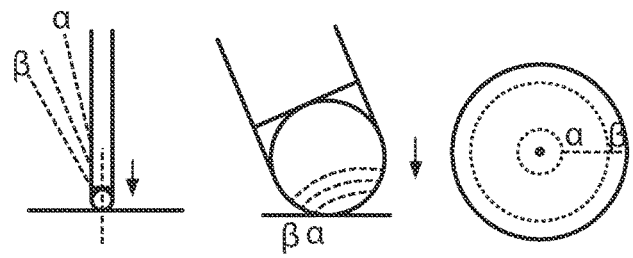
Figure 20A:
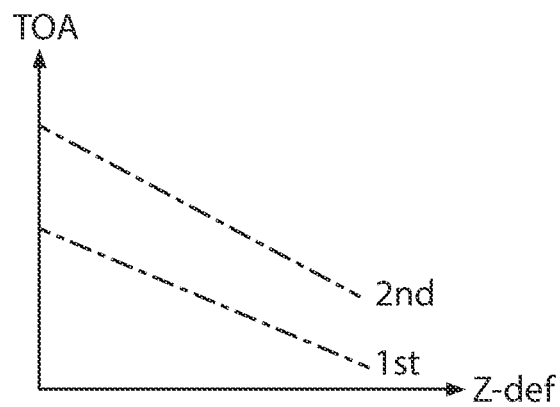
Figure 20B:
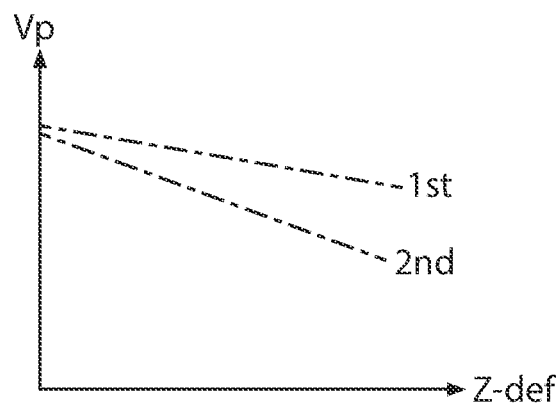
Figure 21:
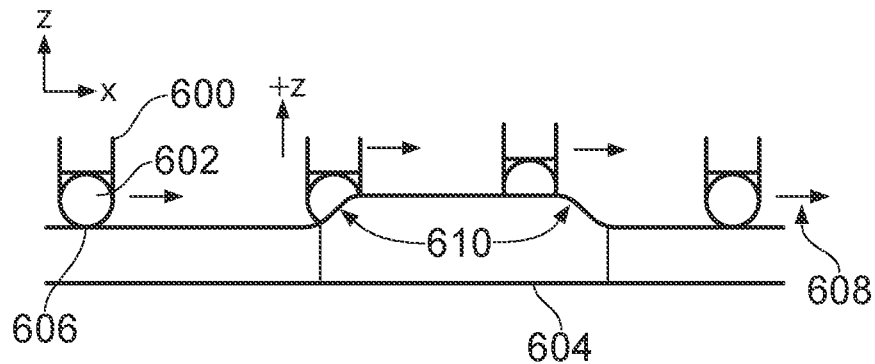
Figure 21:
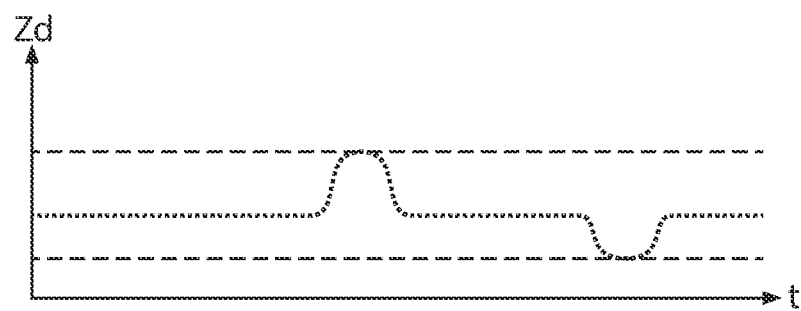
Figure 21:
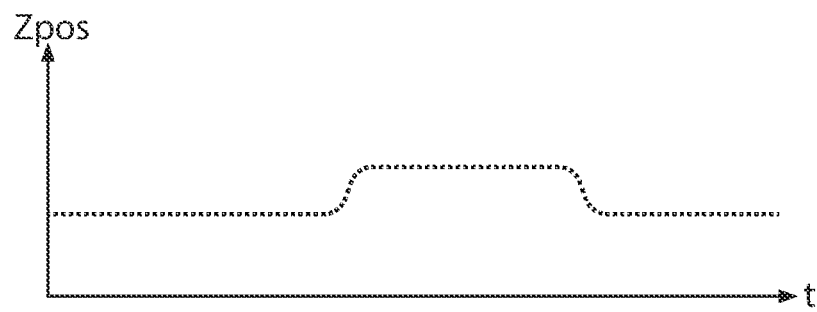
Figure 26A:
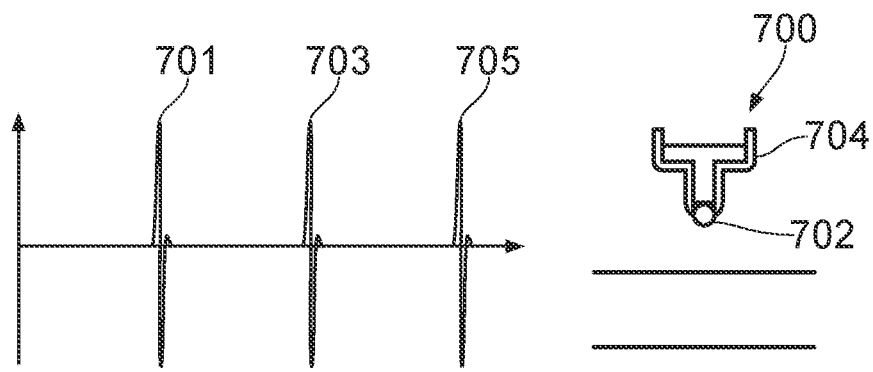
Figure 26B:
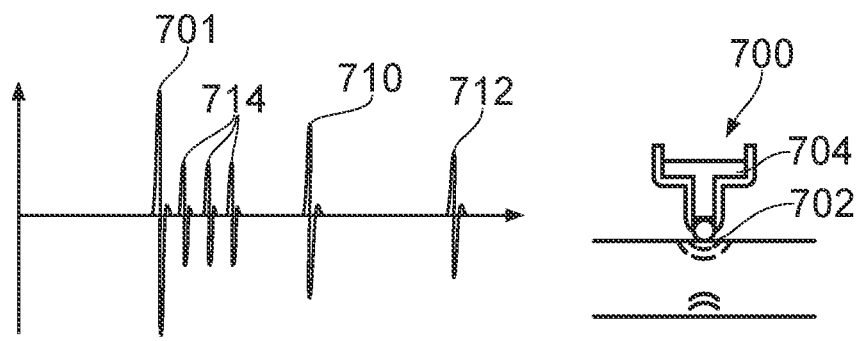
Figure 26C:
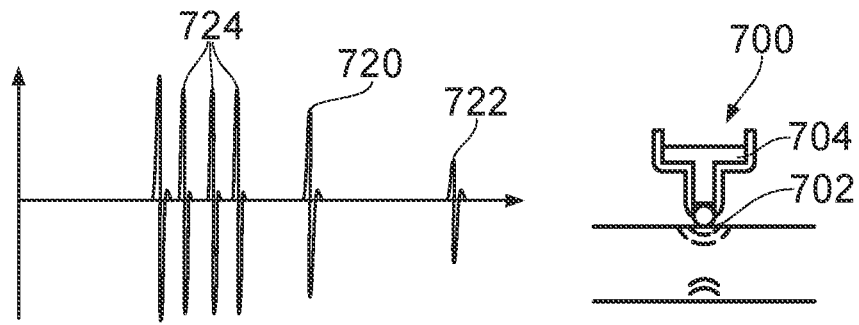
Figure 26D:
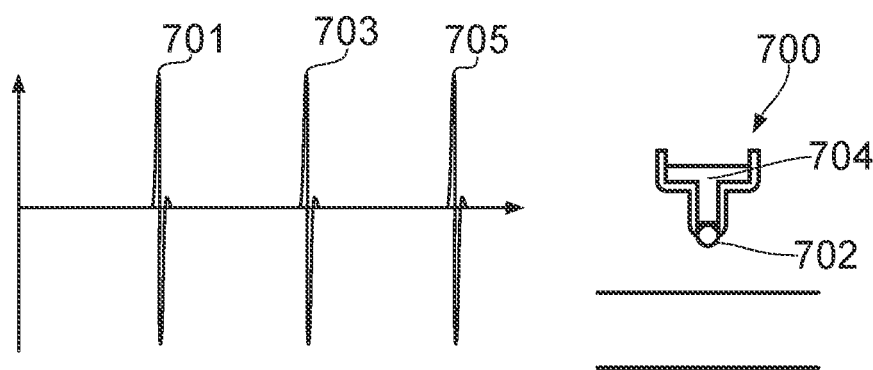
Figure 27:
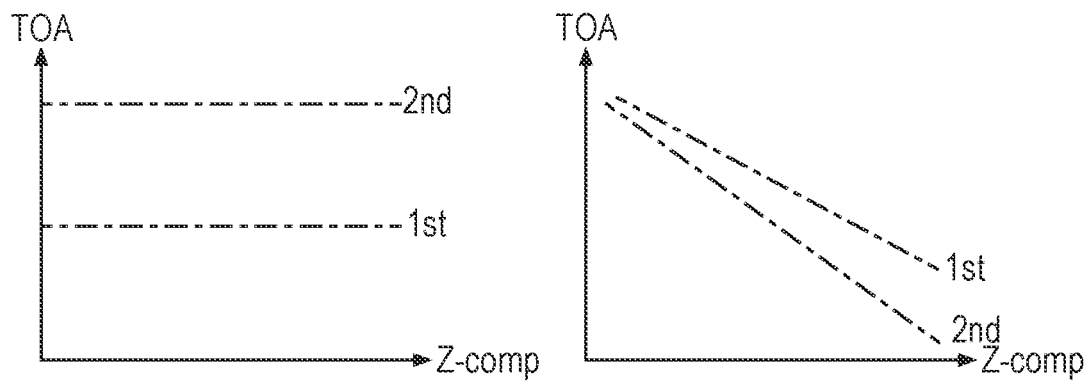
Figure 28:
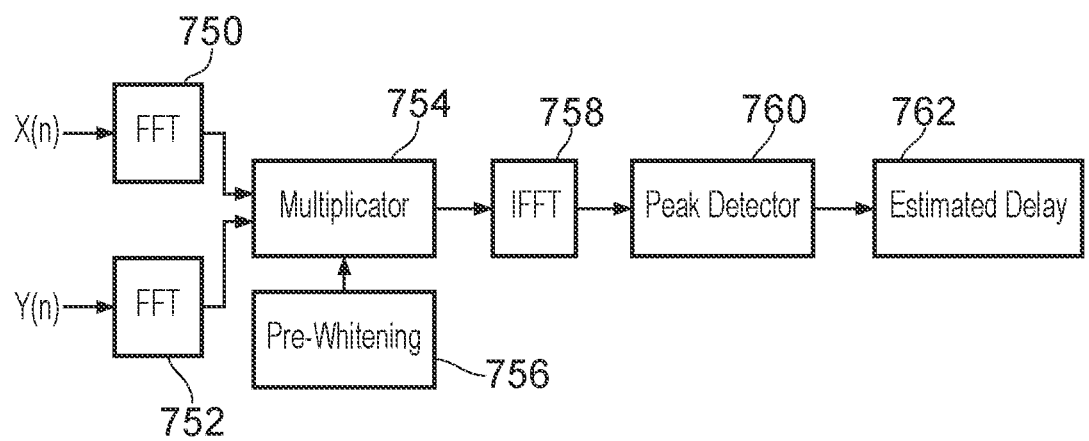
Figure 29:
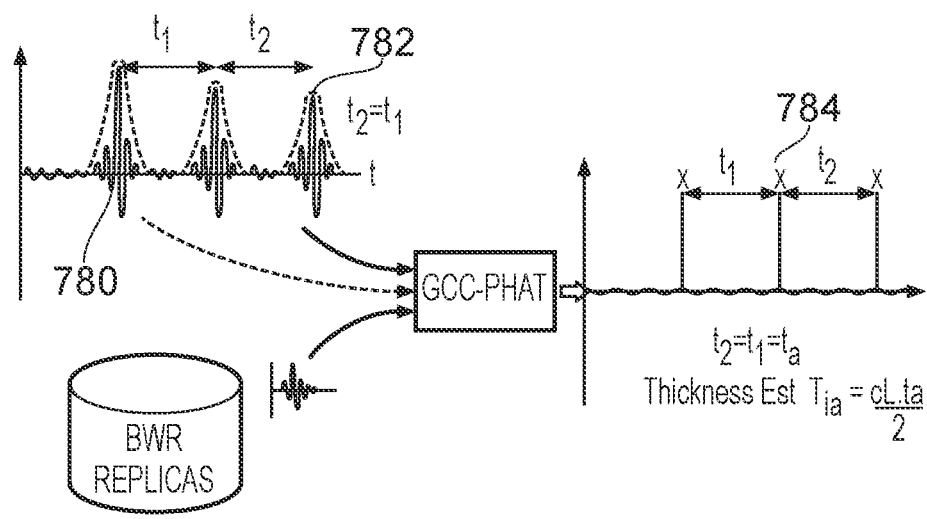
Figure 30:
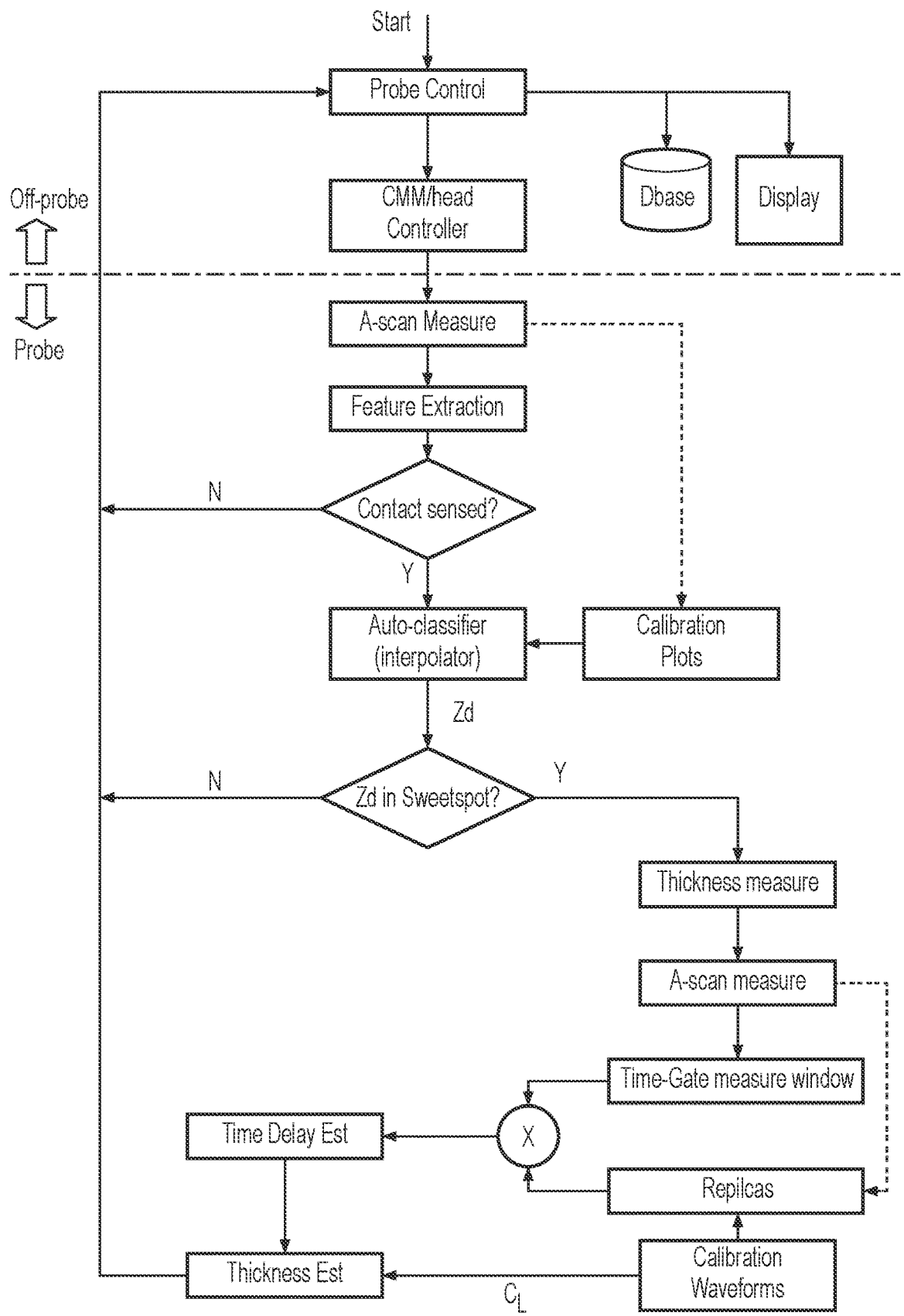
Figure 31:
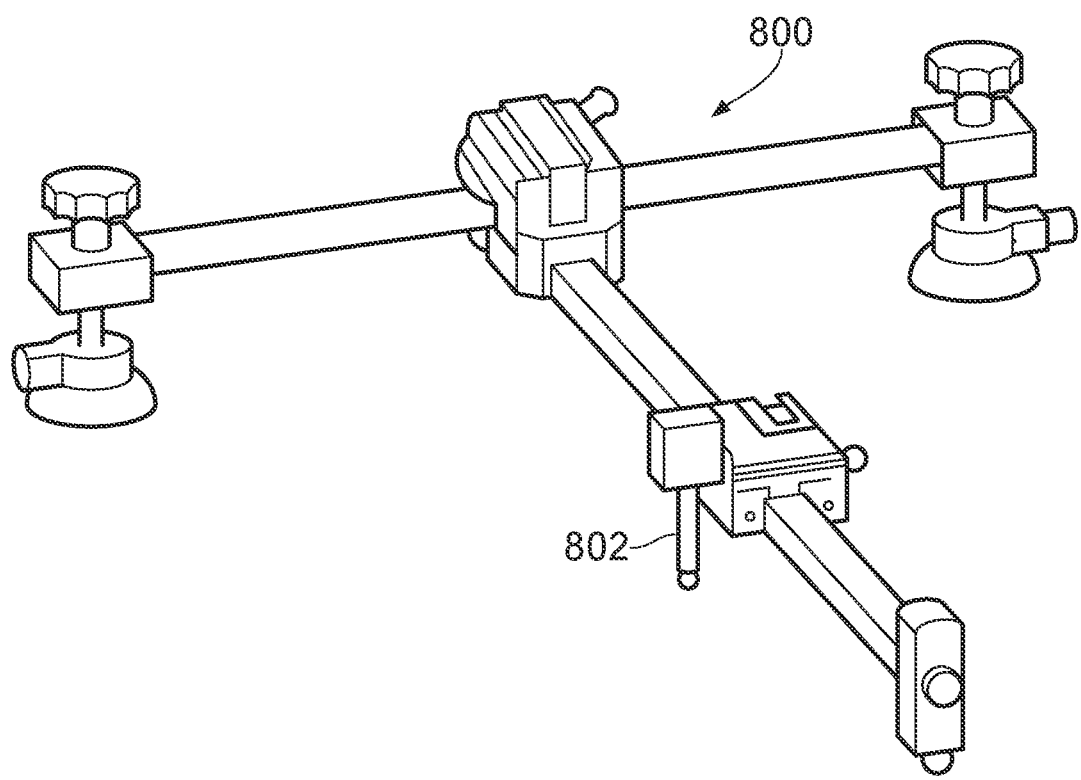
Figure 32:
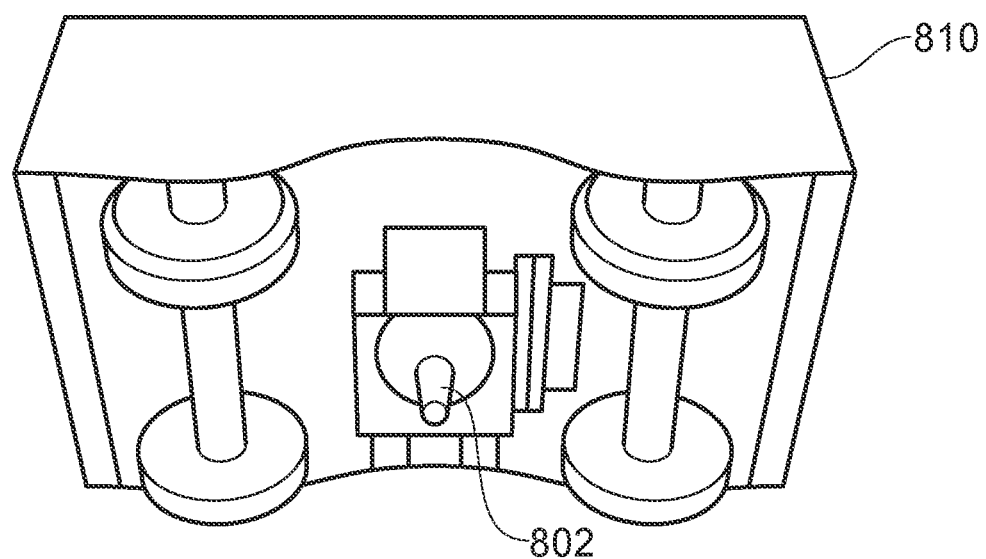

The invention will now be described, by way of example only, with reference to the accompanying drawings in which;

FIGS. 1A, 1B, and 1C illustrate various known ultrasound transducer arrangements, FIGS. 2A and 2B illustrate the principle of ultrasound thickness measurement, FIG. 3 shows a modular ultrasound inspection apparatus mounted on a CMM, FIGS. 4A, 4B, 4C, and 4D illustrate straight and cranked versions of the modular ultrasound probe, FIGS. 5A, 5B, and 5C show a dispensing tray and a plurality of associated coupling modules, FIG. 6 shows in more detail an ultrasound probe comprising a coupling module with a tip comprising a hydrophilic elastomer sphere, FIG. 7 shows the ultrasound probe with a coupling module that provide beam projection normal to the surface of the object being inspected, FIG. 8 shows the ultrasound probe with spherical focusing, FIGS. 9A, 9B, and 9C are images of the coupling module of the modular ultrasound probe, FIGS. 10A and 10B are images of a coupling module attached to a base module comprising an elongate carbon fibre tube, FIG. 11 is an example of a transmit/receive circuit for driving the modular ultrasound probe, FIG. 12 illustrates steps for generating an ultrasound inspection part program, FIGS. 13A and 13B illustrate an ultrasound calibration block, FIG. 14 shows a cranked variant of the modular ultrasound probe scanning a turbine blade, FIGS. 15A, 15B, 15C, and 15D illustrate the A-scan waveforms produced during thickness measurement, FIG. 16 shows the modular ultrasound probe with a hydrophilic spherical tip being brought into contact with the surface of an object, FIGS. 17A and 17B show the deformation of the spherical tip that occurs during the surface contact shown in FIG. 16, FIG. 18 shows the variation of positional information as the spherical tip is moved into the objects surface, FIG. 19 shows the effect of tilt on the sphere centre position, FIGS. 20A and 20B show sphere displacement as a function of ultrasound reflection time of arrival data, FIG. 21 illustrates using the modular ultrasound probe to scan an undulating surface, FIGS. 22A, 22B, and 22C show probe loading scenarios for different parts to be inspected, FIG. 23 shows a modular ultrasound probe configured to measure the bottom surface of a straight bore, FIG. 24 shows a modular ultrasound probe configured to measure the bottom surface of an angled bore, FIG. 25 shows a modular ultrasound probe configured to measure the side walls of a bore, FIGS. 26A, 26B, 26C, and 26D show examples of the ultrasonic waveforms measured during an inspection using an ultrasound probe with a rubber tip, FIG. 27 shows calibration plots of z-axis displacement of the coupling module tip versus reflection peak amplitude attenuation, FIG. 28 is a block diagram illustrating the basic principle of a method for estimating acoustic delay, FIG. 29 illustrates operation of the phase transform replica correlation algorithm that can be employed for improved accuracy in estimating time-delays, FIG. 30 is a flow chart illustrating the steps of a combined surface point and thickness measurement method, FIG. 31 illustrates use of the modular ultrasound probe on an XY scanner, and FIG. 32 illustrates use of the modular ultrasound probe on a self-contained crawler.

Referring to FIGS. 1A, 1B, and 1C a variety of ultrasound probes that comprise longitudinal wave (L-wave) transducers for internal metrology measurements are shown. Such probes have been used previously for inspection purposes, typically as handheld inspection devices.

FIG. 1A shows an ultrasound probe 2 that comprises an outer body 4. An L-wave transducer is provided that comprises an active piezoelectric element 6. The relatively thin piezoelectric element 6 is arranged to have a thickness approximately equal to half the wavelength of ultrasound being generated; this allows the high frequency excitation that is required for accurate rise-time excitation. The piezoelectric element 6 is backed by a thick attenuating backing material 8 to absorb energy from the piezoelectric element 6 and thereby generate the desired heavily damped response in the forward direction. This provides optimal range resolution.

A delay line 10 is acoustically coupled to the piezoelectric element 6 via a wear plate 12. The wear plate 12 protects the piezoelectric element 6. The wear plate 12 has a thickness equal to one quarter of the ultrasound wavelength to enable it to act as a matching layer; this wear plate thickness is preferred because it ensures the waves generated in the piezoelectric element 6 are in phase with those reverberating within the wear plate 12. This means the amplitude of the ultrasound waves within the wear plate 12 and piezoelectric element 6 are additive and maximum energy therefore enters the delay line 10 that is coupled to the wear plate 12. A liquid couplant layer (not shown) is provided at the distal end of the delay line 10 to provide acoustic coupling with the object 14 being inspected. In the example shown in FIG. 1A, the delay line 10 comprises a tapered propagation medium. The propagation medium may be a poly-carbonate resin or cross-linked polystyrene. Fine axial grooves 16 are machined into the sides of the propagation medium in order to suppress internal reflections from within the propagation medium.

FIG. 1B shows an ultrasound probe 20 that has many common features to the probe 2 described above with reference to FIGS. 1A to 1C. The probe 20, however, has a non-tapered delay line 22 that has circumferential corrugation features 24.

The main function of a delay line, such as the delay lines 10 and 22 described with reference to FIGS. 1A and 1B, is to physically remove the ultrasonic excitation far enough away from the inspection surface to temporally resolve the excitation response from the initial reflection from the back wall 26 of the object 14 being inspected. Preferably, this is achieved without any temporal interference from the finite bandwidth excitation pulse ring-down. It can thus be seen that delay lines perform the function of controlling when the ultrasound (i.e. the longitudinal wave) enters the inspection part. Different degrees of tapering can be employed to generate higher contact pressures and accommodate more curved parts. Such tapering also affects the natural focal length and beam divergence (i.e. a diffractive effect) of the device.

Ultrasound probes as described with reference to FIGS. 1A and 1B, provide normal incidence, unfocussed (in the near field) or naturally divergent beam inspections. It is also possible to project ultrasound waves at angles away from the surface normal (e.g. in internal defect detection and sizing). FIG. 1C shows an alternative ultrasound probe that comprises a refractive angle beam wedge 30 (which is sometimes referred to as an ultrasonic shoe). The beam wedge 30 is coupled to the piezoelectric element 6 via a wear plate 12 as per the examples described with reference to FIGS. 1A and 1B. The beam wedge 30 projects the ultrasonic waveforms at an off-axis beam angle from the surface normal of the object being inspected. For such wedge transducers, refraction at the interface between materials of different acoustic impedance is in accordance with the law of refraction (i.e. Snell's Law) and generation of a following shear wave mode (S-wave) at the interface by the phenomenon of mode conversion.

FIG. 1C also shows ultrasound projected from the beam wedge 30 of the ultrasound probe into a metallic part 32. A slower S-wave refracts less from the surface normal N than the faster L-wave mode. Moreover, it is highlighted that the relative proportion of refracted L-wave and following S-wave depends primarily upon the angle of incidence with the S-wave. It is also noted that a significant reflected mode is generated at the interface (i.e. an R-wave is generated) that re-directs spurious acoustic energy within the wedge. An absorbent shell 34 is thus coupled around the propagating wedge material to attenuate this reflected energy. This shell 34 prevents the reflections that would otherwise rebound within the beam wedge 30 and interfere with the reflections of interest from the coupled metallic part 32.

It should be remembered that the ultrasound probes described above with reference to FIGS. 1A to 1C are examples and different designs of ultrasonic delay lines, wedges and lenses have been developed previously to allow optimal acoustic coupling against different solid inspection parts. In the examples outlined above with reference to FIGS. 1A to 1C, it is described how an additional coupling layer (e.g. a layer gel or grease) is provided between the ultrasound probe and the object being inspected. This is because all real inspection parts will exhibit some surface asperities within the micro-structure that cause air-pockets to be trapped at the interface between the probe and the inspection surface. The presence of such air pockets degrades acoustic coupling efficiency, primarily due to the large impedance mismatch between solids and air. The use of a coupling layer, such as a gel, can thus ensure the necessary acoustic coupling efficiency is obtained.

In cases where liquid water or gel cannot be liberally applied to the object being inspected (e.g. in automotive applications), coupling layers in the form of dry-coupling solids have been used previously. Several hydrophilic elastomers (e.g. Aqualene from Olympus) and silicone-rubber based materials (e.g. Ultracouple from Sonemat) are commercially available for dry-coupling ultrasonic non-destructive testing (NDT) applications. However, their coupling performance is not always suited to higher frequency precision thickness measurement probes due to increased L-wave attenuation at the higher probe operating frequency (15-20 MHz). The excessive material stiffness of such materials can also limit close conformity to more curved inspection surfaces. Moreover, silicone based couplant materials are considered to be an unacceptable contaminant within some manufacturing environments (e.g. aerospace).

Referring to FIGS. 2A and 2B, the basic principle of operation of a pulse-echo thickness measurement transducer is outlined. In particular, FIG. 2A shows an ultrasound probe 40 similar to the ultrasound probe 20 described above with reference to FIG. 1B. The ultrasound probe 40 includes a single-element ultrasonic delay line 22 that comprises a dry-coupling polymer pad 42 for coupling to the object 14 to be inspected.

FIG. 2B is an example of the acoustic waveform received by the transducer's active piezoelectric element 6 in response to a transient high voltage excitation pulse being applied across the piezoelectric element 6. This time-domain waveform, referred to as an "A-scan" plot, is more often a time averaged response from a train of such excitation pulses (e.g. a sequence of N pulses where N may be in the range of 16-32) in order to suppress random uncorrelated electronic noise.

The initial excitation pulse generated by the piezoelectric element 6 is labelled as the "Tx-Pulse" in FIG. 2B. This initial excitation pulse causes the inspection L-wave to propagate into the delay line 22 and travel along the delay line at the speed of sound ($C_L$). The first reflection peak (DL1) received back at the piezoelectric element 6 arises from reflection of sound from the distal end of the delay line (i.e. from the interface between the delay line 22 and the polymer pad 42). This reflection from the distal end of the delay line interface (i.e. the DL1 pulse) can be seen to occur at a time well after the initial transmit pulse (Tx-pulse) has completely receded.

Although most of acoustic energy is reflected back at the delay line interface and never enters the inspection part, a sufficient proportion of acoustic energy does transmit into the coupled part 14 as a measurable inspection pulse from which subsequent thickness measurements can be made. Due to the acoustic impedance mismatch between the metallic part 14 (e.g. Z~46 MRayl) and surrounding air (i.e. Z=0.000429 MRayl), the inspection L-wave propagates very efficiently within the part with only very modest attenuation incurred from acoustic leakage across several reflections at the back wall interface. Since the speed of sound within the delay line 22 is low compared to the speed of sound within the thin metallic inspection part 14, multiple reflections between the back wall of the part 14 can occur before a second reflection peak (DL2) from the delay line is registered at the transducer. These back wall reflections thus provide the pulses BW1, BW2, and BW3 that can also be seen in the "A-scan" plot of FIG. 2B. The time window observed within the A-scan between the first and second delay line reflection peak (DL1 and DL2) is thus the probe's primary measurement window.

The thickness of the part 14 may be calculated from A-scan data of the type shown in FIG. 2B in several ways. In practice, such thickness measurements typically involve one of three modes of operation from which the time delay information can be extracted from the measured A-scan. These different modes are typically termed Mode-1, Mode-2 and Mode-3 respectively. In Mode-1 gauging, the time delay measurement is made between the excitation pulse (t=0) and the first back-wall reflection or primary echo from the inspection part. Mode-1 is usually associated with direct contact transducers. In Mode-2 gauging, the time delay measurement is made between an interface echo representing the near surface of the test part and the first back wall reflection. Mode-2 is typically used with a delay line or immersion transducer. In Mode-3 gauging, the time delay measurement is made between two or more successive back wall reflections. Mode-3 is typically used with a delay line or immersion transducer. Mode-3 is most effective where clean high SNR multiple back wall echoes can be observed, suggesting it is most practical in low attenuation high acoustic impedance parts such as fine-grain metals, glass or ceramics. Mode-3 also has the advantage that it does not rely on the absolute time of arrival of back wall or delay line reflections, thus negating the effects of variability in the coupling and delay lines of different coupling modules. Mode-3 also allows parts to be measured that comprise outer coating layers. Any suitable mode (e.g. Mode-1, Mode-2 or Mode-3) could be used as necessary. The use of different modes, possibly with different coupling modules, may also be implemented during a measurement process.

Referring to FIG. 3, modular ultrasound inspection apparatus of the present invention is illustrated mounted on a coordinate measuring machine 50. The CMM 50 comprises a quill 52 that can be moved along three mutually orthogonal linear axes (X, Y and Z). A two-axis rotary head 54, such as the REVO® active head produced by Renishaw plc, is mounted to the quill 52 of the CMM 50. A modular ultrasound probe 56 is in turn carried by the rotary head 54. The ultrasound probe 56, which is shown in an expanded view in the inset to FIG. 3, comprises a base module 58 and an attached coupling module 60. The base module 58 is attached to the rotary head 54 by a standard probe joint that allows the ultrasound probe 56 to be attached to, and detached from, the two-axis rotary head 54 as required. Additional probes, for example, a conventional surface contact (scanning) probe 72 with a ruby tipped stylus can be stored in a probe rack 74 for exchange with the ultrasound probe 56. A calibration artefact 76 is also provided on the CMM bed and in this example a turbine blade 62 held by fixture 64 provides the object to be measured.

As will be explained in more detail below, the ultrasound probe 56 has a modular arrangement. The base module 58 comprises a piezo-electric transducer and wear plate, whilst the coupling module 60 comprises an acoustic delay line and a coupling element for contacting the object to be measured. The modular ultrasound probe 56 is illustrated in FIG. 3 with the coupling module 60 attached to the base module 58. The ultrasound inspection apparatus also comprises a plurality of additional coupling modules 66 that are retained in a storage tray 68 that is placed on the bed of the CMM. In use, any one of the additional coupling modules 66 may be exchanged with the coupling module 60. In other words, any of the additional coupling modules 66 can be attached to the base module 58 and used for measuring internal properties of an object. The process of exchanging the coupling module attached to the base module 58 is performed in an automated manner. For example, a magnet based connection or a screw-thread connection may be employed. The CMM 50 comprises a computer 70 that controls CMM operation and also controls the automatic exchange of the coupling modules.

Figures 4A, 4B, 4C, 4D:
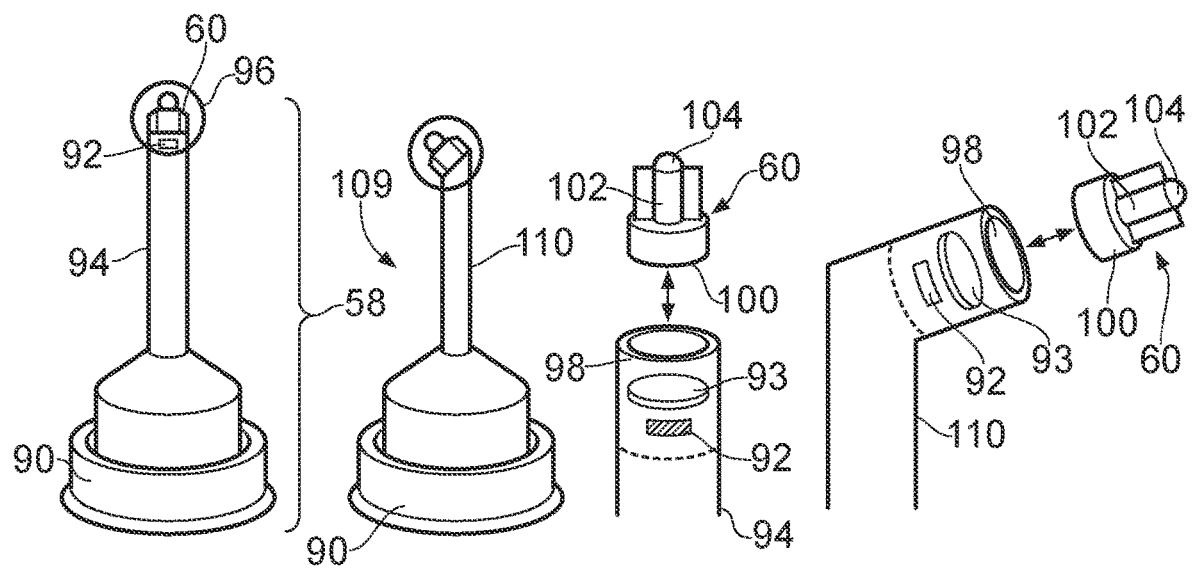

FIGS. 4A, 4B, 4C, and 4D show two examples of modular ultrasound probes that may be used with the CMM described above with reference to FIG. 3. FIGS. 4A and 4B show the modular ultrasound probe 56 that was schematically illustrated in FIG. 3. The probe 56 comprises a base module 58 having a proximal end 90 that can be attached to the rotary head 54 of the CMM 50 via a standard probe joint. The base module 58 also comprises an elongate shaft 94 and includes a piezoelectric transducer 92 having a wear plate 93 located near the distal end of the elongate shaft 94.

FIG. 4B provides an expanded view of the distal end 96 of the modular ultrasound probe 56 shown in FIG. 4A. The distal end of the elongate shaft 94 can be seen to also comprise a first connector portion 98. The coupling module 60 includes a second connector portion 100. The first connector portion 98 and the second connector portion 100 are arranged to allow attachment (and subsequent detachment) of the coupling module 60 and base module 58. In other words, the first connector portion 98 and the second connector portion 100 are complementary connectors that can be releasably linked together. As explained below, this connection may be achieved using a screw thread arrangement or in a variety of alternative ways (e.g. via magnetic linkages etc). The coupling module 60 includes a delay line 102 and a tip 104 for contacting the object to be measured. Attachment of the coupling module 60 to the base module 58 via the first connector portion 98 and the second connector portion 100 causes the delay line 102 to engage the wear plate 93 thereby allowing ultrasound to be coupled from the piezoelectric transducer 92 into the delay line 102 and then into the object via the tip 104.

FIGS. 4C and 4D show a variant of the above described modular ultrasound probe 56. Instead of the base module including a substantially straight elongate shaft 94, the modular ultrasound probe 109 comprises a cranked shaft 110. This provides a different angular orientation of the tip 104 of the coupling module 60 relative to the rotary head 54 and is advantageous for certain inspection processes. The cranked modular ultrasound probe 109 may be stored in a CMM rack (e.g. rack 74 described with reference to FIG. 3) and used instead of the non-cranked modular ultrasound probe 56, as required.

The provision of a modular ultrasound probe as described herein has the advantage that a range of different coupling modules may be attached to the base module. These coupling modules may, for example, provide a range of different coupling properties that can be used for different ultrasound measurements. FIGS. 5A, 5B, and 5C show an example of how multiple coupling modules could be constructed and stored.

FIG. 5A shows in more detail the storage tray 68 described above with reference to FIG. 3. The storage tray 68 comprises a five-by-five array of storage slots 142 (although any arrangement or number of slots could be provided). Each of the storage slots 142 comprises a central hole with two radially extending slots. FIG. 5B shows the winged outer shell 144 of a coupling module that may be placed into and retained by any one of the storage slots 142. An internal surface of the coupling module comprises a screw thread 146 to provide a connector portion that can be screwed into engagement with a complementary screw thread of the base module of the ultrasound probe (not shown). The complementary shapes of the storage slots 142 and outer shell 144 restrict translational movement of any inserted coupling module in the plane of the tray (e.g. XY-plane). Moreover, the wings provided on the outer shell 144 allow the coupling modules to be freely inserted into and extracted from the storage tray 68 in a direction normal to the plane of the storage tray 68 (e.g. via Z-direction movements of the CMM quill) but restrict any rotational movement of an inserted coupling module. The coupling modules can thus be attached to, and detached from, the complementary base module of the ultrasound probe using a rotational (screwing) action. The use of such a screw-fit fastening to provide the modular ultrasound probe is preferred because it allows consistent and suitably good acoustic coupling by providing a consistent and high-tension clamping attachment between the delay line of each individual contact module and the wear plate of the base module. Such screw-fit attachment is also relatively low cost to implement.

In use, the storage tray 68 would be positioned at a known location and orientation on the CMM bed as shown in FIG. 3. The coupling modules would also be placed at known locations (i.e. in predefined slots 142) within the tray 68. In use, the CMM would manoeuvre the base module (e.g. the base module 58 of FIG. 3) to point downwards towards the tray 68 and to be directly above the coupling module that is to be attached to the base module. The base module would then be slowly moved down until it engages the coupling module, whereupon the base module is rotated (e.g. using rotational motion imparted by the rotary head 54 of FIG. 3) so that the two mating threads engage and the coupling module begins to rise out of the tray as it screws on to the base module. The exact point at which the coupling module becomes fully attached and tightly affixed to the base module can be determined by, for example, assessing the ultrasonic response generated during the maneuvering process or by continuously monitoring the torque load placed upon the relevant axis of rotation of the rotary head 54. This torque load can be directly correlated to the electrical current demand placed upon the rotational movement servo motor within the rotary head 54. The rotational angle at which each coupling module is interpreted as being tightly attached to the base module can also be stored. The rotary head 54 can return to this rotational angle to allow the coupling module to be inserted back into a slot 142 in the storage tray 68 and thereafter detached (unscrewed) by the opposite sense of rotational motion than that used for attachment.

It should be remembered that the screw-fit attachment method described above merely represents one possible method for allowing a coupling module to be attached to a base module. There are numerous alternative type of connector that could be employed. For example, the connection could be provided by Luer joints, snap-fit mechanisms, embedded magnetic fixtures etc. A magnetic clamping arrangement could comprise, for example, an assembly of three strong and compact magnets equally spaced around the circumference of the probe tip with polarity "++−" and a matching distribution of three magnets with polarity "−−+" around the perimeter of each coupling module stored in the dispensing tray. This magnetic attachment would provide a simple attachment for coupling module variants and provide only a single possible rotational angle of attachment.

Although the attachment of coupling modules to a base module may be implemented in an automated manner as described above, it should be noted that it would also be possible for such attachment to performed manually by an operator (e.g. by scheduling in a number of set breaks in the inspection sequence), Turning next to FIG. 5C, a variety of different coupling modules 180-191 are described. Each of the coupling modules is contained in an outer PTFE shell having the outer profile shown in FIG. 5B to allow storage in the tray 68 of FIG. 5A. The wear plate 194 of the base module that physically and acoustically couples to the delay line of each attached coupling module is also illustrated.

The coupling module 180 comprises an outer PTFE shell with a Rexolite delay line and a hydrophilic-vinyl-elastomer tip. The coupling module 181 comprises an outer PTFE shell with a Rexolite delay line and a spherical thermoplastic tip. The coupling module 182 comprises a tapered outer PTFE shell with a Rexolite delay line and a curved thermoplastic tip. The coupling module 183 comprises an outer PTFE shell with a Rexolite delay line and a thin latex rubber tip. The coupling module 184 comprises an outer PTFE shell with a hydrophilic-vinyl-elastomer delay line and tip. The benefits of using a hydrophilic vinyl elastomer ball as a tip are explained in more detail below. The coupling module 185 comprises a tapered outer PTFE shell with a Rexolite delay line and a hydrophilic-vinyl-elastomer tip. The coupling module 186 comprises an outer PTFE shell with a Rexolite delay line with an angled distal end to which is attached a hydrophilic-vinyl-elastomer tip. The coupling module 187 comprises an outer PTFE shell with a Rexolite delay line with an angled distal end to which is attached a thermoplastic tip. The coupling module 188 comprises a tapered outer PTFE shell with a Rexolite delay line with an angled distal end comprising a thermoplastic tip. The coupling module 189 comprises an outer PTFE shell with a thermoplastic tip. The coupling module 190 comprises an outer PTFE shell with a stepped distal end for holding a distorted hydrophilic-vinyl-elastomer ball tip that also acts as a delay line. The coupling module 191 comprises an outer PTFE shell, a Rexolite delay line and a thermoplastic material that provides an object contacting tip.

FIG. 6 schematically illustrates how a preferred embodiment of the ultrasound probe that comprises a single hydrophilic elastomer sphere can be implemented. As will be explained in more detail below, such an arrangement can advantageously be provided as part of a modular ultrasound probe.

The ultrasound probe 200 shown in FIG. 6 comprises a single hydrophilic elastomer sphere 208. The hydrophilic elastomer sphere 208 may, for example, be manufactured by synthesis and hydration of a cross-linked hydrophilic vinyl elastomer, super absorbent polymer or hydrogel. The hydrophilic elastomer sphere 208 is contained within an acoustically absorbent shell 212 (e.g. machined from PTFE). The sphere 208, when the probe is loaded onto the surface, becomes uniformly deformed between the wear plate 214 and against the surface 216 of the object 218 being inspected.

A transducer 210 comprising an active piezoelectric element generates L-waves when driven by a train of high-voltage impulsive excitation pulses; e.g. negative going transition (NGT) pulses between 50-150V and of duration ½f. The characteristic acoustic impedance of the sphere 208 (i.e. the "coupling element") is such that there is a sufficient transfer of acoustic energy into it from the transducer wear plate 214 that acts as a matching layer. The relative impedances between the contacting media (i.e. the sphere 208, the inspection part 218 and the surrounding air) determine the proportional acoustic transmission (T) and reflection (R) at the interfaces between the probe and the inspection object in accordance with the equations:

$$R = \left(\frac{Z_2 - Z_1}{Z_2 + Z_1}\right)^2 \quad (1a)$$

$$T = 1 - R \quad (1b)$$

For most thin metallic parts, such acoustic impedance matching issues actually have more influence on the resulting amplitude of the returned reflection echo signals of interest than the inherent acoustic attenuation exhibited within the coupling medium and the inspection part combined. This is because the inherent acoustic absorption that will cause ultrasonic waves to attenuate whilst propagating through any medium is frequency dependent and depends upon a number of factors such as temperature of the medium and the inherent grain structure.

For the example shown in FIG. 6, depicting the interaction of a hydrophilic sphere 208 with an object 218 in the form steel plate, a large proportion (e.g. >80%) of the initial acoustic energy is reflected without ever entering the inspection part 218 due to the significant difference in acoustic impedances between the hydrogel material of the sphere 208 (e.g. 1-3.5 MRayls) and the adjacent steel of the object 218 (e.g. approximately 46 MRayls). However, for the proportion of energy that does propagate into the part 218, multiple reflections at the front and back wall interfaces occur without significant acoustic leakage (i.e. only approximately 1.3% of the transmitted energy from the first back wall reflection is returned to the transducer) and limited fall off in the signal amplitude levels of the repeated back wall reflections.

This example illustrates that selection of the coupling member (i.e. sphere 208 in this example) for mode-3 ultrasonic inspections involves reaching a compromise condition in which just enough energy is transmitted into the part without the coupling being so efficient that too much reflected energy escapes from the part from the first back wall reflection because this would result in a low SNR for subsequent back wall echoes. It has also been found that the large proportion of acoustic energy that never enters the part (i.e. the ultrasound energy that just rebounds within the hydrophilic sphere) can also be measured and interpreted so as to infer something about the physical condition of the sphere within its surroundings or as it interacts with any other solid, gelatinous or liquid bodies. As will be explained in more detail below, analysis of the delay line peaks of the acoustic spectrum that are associated with reflections within the sphere can also be used to establish contact between the sphere and an object. This can be usefully exploited during an automated scan using coordinate positioning apparatus to obtain surface position information. This should be contrasted with the utilisation of A-scan signals from conventional ultrasonic delay line transducers, where such internal delay line reflections are more typically ignored or even time-gated out altogether.

The hydrophilic sphere 208 arrangement illustrated in FIG. 6 has a number of performance benefits, such as allowing both efficient and flexible point inspection measurements and also continuous scanning across a complex geometry inspection surface using a platform with high accuracy yet limited mechanical power. For example, the aqueous (hydrophilic) spheres 208 exhibit negligible acoustic attenuation suggesting that they could be any size. Furthermore, their acoustic impedance value is well suited for ultrasonic transmission into metallic parts. In addition, the incompressible, deformable and almost gelatinous spheres are extremely soft and elastic so as to conform naturally against any reasonably curved inspection surface. Also, the perfectly spherical shape is ideal to achieve sufficient coupling yet retain positional precision in point contact measurements against locally planar inspection surfaces.

The hydrophilic sphere arrangement can also be adapted to provide a degree of useful tapering or a concentrating effect towards the contacting tip potentially altering the effective natural acoustic focal length of the probe. In other words, the elastic hydrophilic spheres can provide a level of control over the beam divergence and direction of the projected ultrasound into the part through accurate manipulation of the probe loading and orientation on the inspection surface. Moreover, the spherical element provides the optimal structural shape to allow such fragile solid material to undergo repeated elastic deformations caused by loading against the inspection surface while retaining mechanical integrity over short-term usage due to an even distribution of loading stresses as the spheroid is compressed between the planar wear face and the inspection surface. It is noted that the incompressible spheres preferably reside quite loosely within the shell and can elastically deform under load many times, each time returning to a perfect sphere after removing the load. It is only when some tearing or splitting occurs at the sphere surface that the element disintegrates.

The hydrophilic sphere 208 arrangement illustrated in FIG. 6 also has the important advantage that the water swelling chemical property of the hydrophilic polymer spheres allows them to release a controlled amount of water from the external surface. The amount of water released is typically of a quantity that will evaporate readily within the atmosphere. This subtle water release substantially improves acoustic coupling across all inspection surfaces since the water displaces unwanted air-pockets trapped between the probe and the surface rough micro-structure. This is done without leaving any obvious residual liquids or contaminants and the need to apply gel couplants to the part is removed. Moreover, this water expulsion can be controlled through known organic synthesis methods and, as such, it also provides the additional benefit that it is possible to continuously scan the ultrasonic probe across an inspection surface without losing contact. More specifically, tangential forces introduced by any lateral motion of the scanning probe across the inspection surface (F) would in turn induce significant frictional resistive forces (N) in the contacting sphere that could potentially impair the positional precision of the moving probe or cause premature mechanical failure, if the coupling member was totally dry. However, through the controlled water sweating properties of the hydrophilic spheres, sufficient liquid is released from the sphere to act as a natural and effective lubricant facilitating smoother continuous scanning motion across most surfaces in any direction.

The hydrophilic sphere based arrangement described with reference to FIG. 6 can thus be seen to offer a number of benefits with respect to efficient point inspection and continuous automated scanning applications. For certain geometries, e.g. involving non-parallel front and back walls and/or where there is limited access, it may not always be practical or even physically possible to measure such parts by inducing L-wave beam refraction at the inspection surface at the required refractive angle solely through re-orientation of the probe relative to the surface. In addition, irrespective of the natural focal lengths and refractive beam angle produced by the aperture and probe orientation against the surface, the projected beam is inherently divergent and only focused naturally as a result of the aperture size and operating frequency, without any explicit near-field refractive focusing. Furthermore, although water release from these fixtures can be controlled and is extremely modest, some applications (e.g. inspection of car assemblies) may require there to be no liquid residuals including water. It is therefore advantageous to alternatively or additionally provide coupling modules that comprise a rigid plastic refractive lens or angle beam wedge material (e.g. acrylic or Polystyrene) bonded to a suitable soft coupling layer that forms the object contacting tip. This "compound class" of coupling modules enables selective yet rigidly fixed acoustic beam patterns to be generated by the ultrasound probe.

Referring to FIG. 7, an example of a compound design of coupling module is shown. Again, the example shows the underlying principle of operation and could be implemented in the modular ultrasound inspection apparatus described above. The ultrasound probe of FIG. 7 comprises a piezoelectric element 248 coupled to a normal incidence tapered delay line 250 that is bonded or loosely coupled to a thin soft coupling layer 252 that protrudes and thus provides an object contacting tip. The coupling layer 252 in this example is a thin layer of latex rubber, for example as used to make surgical gloves or similar items. Alternatively, the coupling layer 252 could be provided by a compressible oil-based thermo-plastic. Both latex rubber and oil-based thermoplastics can be produced that generate no residuals from deformation so would generate no liquid contamination during an inspection. When firmly loaded and acoustically coupled to the inspection surface, the normal incidence compound ultrasound probe will generate a fixed known natural beam divergence 256 within the part 254. However, a rigid refractive element can be specifically shaped asymmetrically in order to refract (i.e. steer) the L-wave at a set angle from the normal in order to accommodate more complex internal geometries. This is in accordance with Snell's law of refraction and methods may also be used to filter the slower shear wave modes.

FIG. 8 shows a further example of a compound design of coupling module. Again, the example shows the underlying principle of operation and could be implemented in the modular ultrasound inspection apparatus described above. The ultrasound probe of FIG. 8 comprises a piezoelectric element 260 and a plastic planar-concave lens 262 that forms a rigid refractive element. The planar face 264 of the lens 262 is coupled to the transducer wear plate 266 and the spherically concave face 268 is coupled against (i.e. "cupped around") a hydrophilic elastomeric sphere 270. The refractive element (i.e. the planar-concave lens 262) may alternatively be shaped as any required type of acoustic lens to concentrate or focus the L-wave acoustic wavefront within the part at a point in the near-field. The ultrasound probe of FIG. 8 allows, given the relative sound speeds within each medium, the L-wave to be focused within the part 272. For example, the L-wave may be focused at point P on the back wall of the part 272. This arrangement provides a similar A-scan response to that obtained using a spherically focused probe of an immersion system; the hydrophilic elastomeric sphere 270 replaces the water in which the probe would be submerged.

FIGS. 9A, 9B, 9C, 10A, and 10B are various design images and photographs of components of a modular ultrasound probe of the type described above that comprise a coupling module having a coupling element in the form of a hydrophilic elastomeric sphere.

As explained above, the modular ultrasound inspection apparatus described above comprises a plurality of coupling modules that can be attached to a common base module. FIG. 9A shows a design image of the distal end of the base module 290. The cylindrical body of the base module includes on its outer surface a threaded connector portion 292. As will be explained below, the threaded connector portion 292 allows suitably arranged complementary coupling modules (e.g. as shown in FIGS. 9B and 9C) to be screwed onto the base module.

Turning to the coupling modules, the coupling element (e.g. an hydrophilic elastomeric sphere) that touches the part to be inspected and any required delay line (e.g. a normal delay medium or a refractive delay medium) is preferably retained within an acoustically absorbent shell. The provision of such a strongly absorptive shell means that projected L-waves being used for the thickness measurements can dominate over other waves (e.g. reflected waves from the sides of the coupling element). This can, for example, result in more compact refractive wedge designs being possible. Examples of absorptive shells for housing a hydrophilic elastomeric sphere will now be described with reference to FIGS. 9B and 9C, but it should be noted that similar absorptive shells could also be used for different types of coupling elements.

FIG. 9B shows a base module 293 made to the design illustrated in FIG. 9A and attached to a coupling module 295 comprising an acoustically absorbent shell 294. The shell 294 suppresses internal acoustic reflections and retains a hydrophilic elastomeric sphere 296. In this example, the shell 294 is precision-machined in glass-filled PTFE (e.g. PTFE sold under the Teflon® brand). Alternatively, pure PTFE or some other suitable anechoic polymer could be used. It should also be noted that a range of acoustic polymers specifically designed for anechoic absorption of high frequency acoustic reflections are commercially available. For example, Aptflex F28 from Precision Acoustics is a high frequency anechoic acoustic absorber material used for test tank linings within immersion systems and would thus be a suitable material for the absorbent shell as it offers extremely favourable acoustic attenuation attributes for any unwanted internal ultrasonic echoes. However, PTFE has the advantage of being a low friction material that is ideal for allowing the hydrophilic spheres to move freely within the shell as it compresses under loading on the surface, without any tendency to stick to the inner surface of the restraining shell. An internal screw thread (not visible in FIG. 9B) forms a second connector portion that allows attachment of the coupling module 295.

FIG. 9C illustrates a compound coupling module 300 formed from a shell 302 that encases a delay line 304 and retains a hydrophilic elastomeric sphere 306. The shell 302 is, like the shell 294 illustrated in FIG. 9B, formed from a precision-machined in glass-filled PTFE. An internal screw thread 308 forms a second connector portion that allows attachment of the coupling module 300 to the first connector portion comprising the complimentary screw thread 292 formed on the base module 290.

As shown in FIGS. 9A and 9B, the PTFE shells 294 and 302 encase the majority of each coupling module with only a fraction of the hydrophilic elastomeric spheres 296 and 306 that provide the coupling element protruding from the end of the shells in order to make direct contact with the inspection surface. In the case of the compound coupling module 300 of FIG. 9C, the detailed shape of the PTFE shell 302 in the vicinity of and around the circumference of the protruding soft hyper-elastic coupling material of the delay line 304 has an effect upon the coupling performance achieved due to the effective compressive restraint of the soft coupling element 306 as it is trapped within the structure. It also has an effect on the likely service-life of the consumable item due to an increased probability of tearing the hydrophilic elastomeric sphere 306 in cases where this restraint causes a concentrated stress profile across the soft coupling material. It is also noted that the PTFE shell provides some useful general protection to soft perishable coupling materials.

The use of glass-filled PTFE to form the shells 294 and 302 of FIGS. 9B and 9C respectively also aids attachment of each coupling module to the associated base module. In particular, the PTFE allows smooth, automated screw-fastening between each coupling module and the base module. The mechanical screw-fit assembly can thus be designed using materials (e.g. a PTFE shell for the coupling module and steel for the base module) that promote smooth interaction between the mating parts. Moreover, the coupling module dimensions can be set so that when the screw-fit assembly becomes tight the planar wear face or wear plate within the base module makes consistent contact with an adequate clamping tension force with the inner coupling material of the coupling module. The use of such a PTFE shell allows the formation of delay lines without the need to micro-machine grooves to suppress reflections, allowing cheaper high volume injection moulding or vacuum casting manufacturing methods to be adopted.

Referring to FIGS. 10A and 10B photographs of one embodiment of the ultrasound probe 330 are provided. The ultrasound probe 330 shown in FIGS. 10A and 10B is configured to be attached to a rotary head that is in turn mounted on the moveable quill of a CMM. In particular, the modular ultrasound probe shown in FIGS. 10A and 10B is arranged for attachment to a two-axis rotary head (e.g. a REVO® head of the type described above with reference to FIG. 3). It would, of course, be possible to attach such an ultrasound probe to other measurement systems.

The ultrasound probe 330 comprises a base module that includes a main body portion 321 that contains all the transmit-receive (Tx-Rx) electronics required to drive the piezo-electric ultrasound transducer and digitally record the acoustic response to such excitations. The main body portion 321, which is provided at the proximal end of the probe 330 that attaches to the CMM comprises optional electromagnetic shielding to protect the transmit-receive electronics. The main body 321 can also contain all the electronics required to power the probe and communicate control data and activation commands to the probe (e.g. to schedule ultrasonic measurements). Power and/or control data, including ultrasonic data and thickness measurement results, may be passed through the rotary head communication channels.

The main body 321 also comprise a thin, elongate and rigid carbon-fibre tube 323 that extends along the probe's axial length. The distal end of the tube 323 carries the ultrasound transducer and a first connector portion 322 for attachment to a coupling module. FIG. 10A shows the base module without a coupling module attached, whilst the enlarged FIG. 10A shows a coupling module 332 attached (i.e. screwed onto) the first connector portion 322. A high-frequency and shielded coaxial cable (not shown) extends internally along the carbon-fibre tube 323 so as to electrically connect the Tx-Rx electronics in the main body 321 to the transducer provided near the tip. This transmits the high voltage pulses from the Tx-pulser electronics to the transducer in order to generate acoustic waveforms and also carries the measured analogue voltage signals from the transducer back to the Rx-electronics to be digitised and recorded. Although the physical form of the probe is advantageously chosen so that the electronics module is compact and contained within the main body close to the CMM's measurement head, the overall length can be specifically selected by varying the length of the carbon-fibre tube and/or the crank angle so that the transducer module and probe tip can access hard-to-reach part geometries.

Referring to FIG. 11, the transmit-receive (Tx-Rx) electronics contained within the main body 321 of the ultrasound probe 330 described with reference to FIGS. 10A and 10B are described.

FIG. 11 depicts one embodiment of the analogue and digital electronic modules that can be provided within the ultrasonic probe. An analogue "pulser" circuit 350 is provided that is capable of generating repeated trains of high voltage (50-150V) a.c. analogue signals (e.g. NGT pulses). Although the pulser 350 is provided, a more sophisticated digital waveform synthesizer could alternatively be employed to generate frequency or amplitude modulated waveforms to drive the piezo in more attenuating environments. The high voltage pulses generated by the pulser 350 effectively drive the piezoelectric active element 356 within the transducer of the probe to output the required ultrasonic waveforms 358, but without exceeding the maximum voltage for such a thin fragile piezoelectric element. Each pulse activation may be instigated and precisely controlled in time by an enable signal sent to the "pulser" circuitry 350 from an FPGA 352 or equivalent processor. For every activation, a fast T/R switch 354 allows the device to instantaneously switch between the transmit mode and the longer duration receive mode during which time the system acquires and digitally records the acoustic response to the transmitted pulse measured by the reciprocal piezoelectric element 356.

The amplitude level of the received signals of interest can vary significantly, so a variable gain amplifier (VGA) 360 is optionally provided to induce SNR gain across the acquired A-scan response in order to amplify the signal prior to digital acquisition. Moreover, to equalise the variability within each A-scan response due to propagation loss or attenuation with some materials, a form of automatic gain control (AGC) known as distance-amplitude correction (DAC) may also be implemented. The amplified A-scan is then digitized using a suitably wide dynamic range (e.g. 12 bit) analogue-to-digital converter (ADC) 362 where sufficient over-sampling above the Nyquist rate is provided as the sample rate fundamentally effects the temporal resolution of the measurement system and thus the accuracy of the thickness measurement; e.g. a sampling rate of 125 MHz or higher may be suitable for a 20 MHz transducer. The encoded digital waveforms from the ADC 362 may also require band pass filtering using a digital filter, for example a low order FIR with a pass band matching the operating frequency of the transducer. The Tx-Rx electronics are designed so as to minimise all possible sources of electronic noise that may be observed within each individual A-scan. Such uncorrelated noise is most effectively suppressed by averaging across N successive repeated A-scan measurements (ie. providing a theoretical IN SNR gain).

Referring to FIG. 12, an example will now be described of the input data requirements for inspection planning software that is employed to compile a sequence of automated movement instructions for the CMM and ultrasound inspection apparatus described with reference to FIG. 3.

It is known in surface contact metrology using a surface contact (scanning or touch trigger) probe to employ software that utilises nominal CAD data models of the inspection part to automatically generate a part program that plans and executes the measurement moves. For example, high-resolution continuous sweep scan measurements of a turbine blade can be performed using the ApexBlade software sold by Renishaw plc to generate a part program in the industry standard DMIS language for controlling the CMM. Similar CNC software, for example using and generating accepted high-level CMM control software languages (e.g. DMIS), may also be used to automatically plan and schedule the ultrasonic probe inspection. Any such inspection plan, whether performed automatically or manually, preferably includes some form of detailed part-specific inspection planning or scheduling.

A first requirement is to define where the ultrasound measurements are required. This may be achieved by defining, prior to ultrasonic inspection, an inspection plan that defines the position of all measurement nodes, linear sections (B-scan lines) or defined inspection areas across the target inspection part upon which ultrasonic inspection measurements are to be taken. This process may use external form measurements of the inspection part performed using a surface contact measurement probe of known type. After defining the measurement nodes and with knowledge of the detailed inspection part geometry and the available mechanical degrees of freedom offered by the automation platform carrying the ultrasound probe, the type of ultrasound probe required for the measurements can be determined. For example, it might be possible to use only a normal axis ultrasound probe (e.g. as described with reference to FIGS. 4A and 4B) or a crank-angled ultrasound probe (e.g. as described with reference to FIGS. 4C and 4D) may be necessary for some or all measurements. If more than one ultrasound probe is required, an automatic probe changing routine may be required.

As explained above, the modular ultrasound probe includes an exchangeable coupling module. As shown in FIGS. 3 and 5A, the coupling modules may be stored in a storage tray and hence be automatically attached to, and detached from, the base module of the ultrasound probe as required. The inspection plan may thus include selecting the coupling module or modules that are most beneficially employed for measurements across different geometries within the inspection part. Each coupling module may also have a limited lifetime (e.g. it may be a consumable or limited lifetime item) and the planning process may thus include a replacement strategy for refreshing such coupling modules. For example, a purely scheduled changing strategy would likely involve deciding upon the optimal coupling module for each section of the part in terms of coverage and scan performance and scheduling a set number of replacements within the inspection to eliminate the possibility of using a damaged coupling module. A predictive replacement strategy would involve replacement of a coupling module only when damage or sub-optimal performance is detected; this would preferably involve determining the optimal designs for a specific geometry and ensuring that enough of each design is available to cover the likely number required. A mixture of scheduled and predictive replacement could also be employed.

After determining the measurement nodes, ultrasonic probe changes and coupling module changes for the planned inspection, the optimal movement paths can be generated. This process preferably ensures that the probe movements are suitably blended together so that the probe does not collide with any obstacles (e.g. the part, fixturing or granite bed). For a predictive coupling module changing strategy, it is important that wherever the probe is located within the measurement volume when damage is detected to the current coupling module, a safe movement path sequence can be called in order to return the probe to the storage tray. A list of the internal wall thickness measurement nodes on the inspection surface can then be compiled and the ultrasound path defined.

After attaching the base module of the ultrasonic probe to the moveable member (e.g. two-axis rotary head) of the CMM, tests may be performed to ensure that the piezo probe is functioning correctly. The axial alignment and position of the base module when attached to the rotary head can be assumed to be consistently fixed with sufficient accuracy to automatically attach and detach coupling modules from a storage tray. This is because the base module of the modular ultrasonic probe is a substantially rigid body and can be attached to the measurement head using established kinematic joints. However, calibration of the position of the coupling element (i.e. tip) of the coupling module is preferably performed after attachment of a coupling module to the base module. This is in order to accurately determine the position of the sensing tip (i.e. the coupling element) within the coordinate system of the CMM.

FIGS. 13A and 13B show an example universal calibration artefact that can be used for sound speed calibration, XY positional calibration and other calibration tasks. It should be remembered that this is merely one example of a suitable calibration artefact and other calibration artefacts and techniques may be used instead.

FIG. 13A shows a two-dimensional cross-sectional representation of the calibration block 400 that is also shown in three-dimensions in FIG. 13B. The calibration block 400 is a precision machined artefact that incorporates planar orthogonal faces 402 so that it can be placed on the bed of a CMM and its position accurately measured (i.e. datumed) in terms of XYZ position and orientation using a surface measurement (scanning or touch trigger) probe. The block 400 also has a flat planar top surface 404 with a central dimple feature 406 that can be located in the CMM volume using a surface contact (e.g. a touch trigger or scanning) probe. The calibration block 400 is hollow and contains an internal conical surface 408 with a shallow slant angle (e.g. 5-10 degrees) relative to the top surface plane 404. The apex of the cone defined by the conical surface 408 is concentric to the XY coordinate of the central dimple feature 406.

In use, the position and orientation of the calibration block 400 in the coordinate system of the CMM is determined by a conventional metrology datuming process. For example, a datum point and the principle axes can be determined from a orthogonally planar section of the block by taking at least 6 touch points (e.g. three points defining the Z-plane, two points defining an x-line and one point defining a Y-point) using a conventional touch trigger probe. Once the position of the calibration block has been found in this manner, the position of the ultrasound probe tip within the CMM volume can be determined.

In particular, the position of the block 400 within the CMM volume can also be determined from two sets of measurements taken using an acoustic probe comprising a coupling element in the form of a hydrophilic elastomeric sphere. In the first measurement, the position of the tip of the acoustic probe (and hence the position of a point on the surface of the block) is determined in the z-axis by moving the acoustic probe to point downwards to a point above the top plane of the calibration block 400. In other words, the probe is moved in the [0 0 −1] direction by nulling the head to face the top face normal vector [0 0 1]. The acoustic probe is then loaded down onto the top planar surface 404 of the block 400, which resides at a known Z-height, by slowly moving the CMM quill down in the Z-direction. By repeated loading of the probe on to and off the top surface 404 it is possible to estimate the Z-coordinate at which the probe makes tangential contact with this surface; this is achieved by analysis of the acoustic signal generated from reflections from the hydrophilic elastomeric sphere as described in more detail below. This first measurement thus enables an accurate determination of the Z-position of the tip within the CMM volume.

Secondly, to estimate the XY location of the tip of the acoustic probe within the CMM coordinate system, a sequence of ultrasound thickness measurements (e.g. at least 6 for a unique solution) are made across the top surface 404 of the calibration block 400 above the internal conical feature. Again, the probe is arranged to point downwards (i.e. by nulling the probe head) and the XY position of the probe is recorded at each measurement node. The block thickness is then calculated at each measurement point and the set of thickness measurements acquired in 3D are mathematically fitted to a conical shape, for example using the Levenberg-Marquardt (LM) algorithm or any linear or non-linear least-squares conical fitting algorithm. This fitting process reveals the offset between the XY estimation of the apex of the fitted cone and the actual XY location of the dimple.

In a preferred embodiment, the calibration block 400 shown in FIGS. 13A and 13B may be machined using the same type and grade of metallic material found in the part to be inspected. The block 400 can then also be used to perform sound speed calibration in order to estimate the wall thickness of any subsequent part measurements. This can be achieved by measuring the time delay for the known thickness sections around the perimeter of the calibration block. It is noted that sound speed may alternatively be measured directly from known solid sections of the part to be inspected (e.g. on the root of a blade or near the aerofoil) so as to minimise variability sources. This is because the sound speed calibration likely provides the largest source of measurement error within the thickness measurement calculation; e.g. due to temperature differences within the environment, crystallographic orientation or differences in density/porosity microstructure.

Mode-3 gauging is a preferred method for thickness calculation using the modular acoustic probe described above as it is substantially unaffected by variability in the coupling element (e.g. variations in the propagation path through the hydrophilic elastomeric sphere). However, the calibration techniques described above can also be used in mode-1 or mode-2 gauging. In such gauging techniques, absolute propagation time delays for the first back wall reflection across a range of thicknesses can be used to directly obtain any subsequent thickness measurements within the measured range by linear interpolation. This may have a limited number of uses, for example measuring much thicker and more highly attenuating parts with a coupling module having a rigid constant delay line and a very thin coupling element (e.g. latex rubber) so as to reduce variability.

The calibration block 400, which may represent accurately the part being inspected, can have further uses within the context of highly automated point measurement and continuous scanning. As described below, these additional uses include probe contact detection, normal probe loading estimation, thickness measurement and wiggle movement adaptation.

For probe contact detection, the calibration block 400 provides a convenient known geometry and identical planar surface target from which the probe with any coupling module attached can measure and calibrate relevant variations in the A-scan waveform for the probe, at the point when the tip comes into contact with the surface. As will be described in more detail below, this technique exploits changes in amplitude, phase, fine-scale shape, frequency and/or time of arrival (TOA) of the internal reflection echoes from within the coupling module which are extracted from a continuous repeated train of measured A-scans so as to infer probe tip contacts with any solid body. For example, it has been found that the amplitudes of second and third delay line reflections (DL2 and DL3) within a rigid delay line are extremely sensitive to any probe tip contacts from a solid body.

For normal probe loading estimation, the use of internal reflections from the coupling modules extracted from a repeated train of A-scans to infer such probe tip contacts can be extended to measure and calibrate the normal loading of the probe on to a planar surface, using such a calibration block. By loading the probe slowly on to the calibration block whilst continuously recording A-scans at a high rate, waveform features from the coupling module's internal reflection echoes as the soft coupling element deforms against the inspection surface can be extracted and stored with the positional information of the tip and surface. These features adequately define how the physical condition of the soft coupling element within the coupling module changes under normal loading conditions and can therefore infer the loading condition when making subsequent measurements across the inspection surface. Such normal loading calibration to infer displacement or deflection within the soft coupling element of the coupling module can be very useful for ensuring precise manipulation of the probe against the inspection surface (e.g. to alter the effective aperture or angle of incidence of the probe) or for continuous scanning of the maneuvering probe across complex and/or unknown geometry surfaces. Substantially constant loading conditions across an unknown topography can thus be attained using such inferred measurement at a high rate as direct feedback for positional adaption in the CMM and/or active head controller.

For thickness measurement, accurate and computationally efficient time delay estimations between back wall reflection echoes are possible. In a preferred embodiment, this time delay estimation process can involve implementation of a form of generalised cross-correlation (GCC) algorithm that convolves stored or extracted replicas of back wall echoes across the measured A-scan in order to accurately sharpen the time delay estimation between successive back wall reflections. This spectral technique exploits the overall shape of the back wall reflection waveforms including amplitude and most notably phase (e.g. using phase transform pre-whitening) to determine their time of arrival and thus the accurate time difference between successive echoes. As such, the calibration block 400 can be used to measure and store an extended set of representative replica waveforms of back wall echoes that can be used during the inspection. It should also be noted that the same methods for measuring the time delay between successive back wall reflections in Mode-3 gauging can be used for precision measurement of the internal reflection echoes from the deformable coupling modules. More specifically, it is beneficial to store template signatures of the internal reflection peaks during calibration that can be used during the subsequent inspection to extract the accurate time of arrival of the internal reflection peak.

For wiggle-movement adaption, it is identified that ultrasonic coupling to any surface is not entirely deterministic in that the best SNR is not always achieved for a normal incidence L-wave transducer simply by loading the device normally to the surface with the maximum force available. Stochastic processes can also influence the SNR achieved for a probe being loaded on to an inspection surface. For example, the prevailing micro-structure, humidity and temperature conditions can influence how air becomes trapped between the probe and the inspection surface, introducing significant potential variability in the ultrasonic transmission. For these reasons, it is known in both manual and automated ultrasonic NDT measurements (e.g. using the Marietta-NDT 5-550 system) to apply some fine-scale adaption to the probe orientation (e.g. rolling and/or twisting), whilst keeping the probe tip stationary on the surface, in order to optimise the received signal level. Moreover, with an accurate and infinitely indexing automation platform (e.g. a CMM with a 5-axis active head), it becomes possible to determine favourable sequences of such fine-scale probe movements (e.g. rolls and twists) for a specific inspection condition. It is therefore further highlighted that the calibration block 400 provides such a known and representative surface in which the probe can determine or algorithmically learn (e.g. using optimisation, clustering or artificial neural classifiers) the optimal fine-scale sequence of wiggle movements for a modular acoustic probe that can then be adopted during the subsequent part inspection.

FIG. 14 illustrates a process for measuring an aerospace fan blade disc/hub 450 using five-axis CMM apparatus of the type described with reference to FIG. 3 and the crank-angle variant of modular acoustic probe 109 illustrated in FIGS. 4C and 4D.

After the modular acoustic probe has been mounted to the two-axis rotary head of the CMM and the necessary calibration procedures completed, the probe 109 can be used to take measurements across the part. The probe 109 can take both point measurements 441 and continuous scanning measurements 442 during the inspection of the blade 450, as necessary. For example, measurements may be taken at a set of spatially distinct nodes (e.g. at twenty locations distributed across each blade) and/or continuous scanning measurements may be acquired (e.g. by moving the probe along a path on the blade's surface whilst collecting measurements at a 1 mm pitch).

As shown in FIG. 14, the crank angle allows the ultrasound transducer (and hence the projected L-waves) to be orientated at a fixed angle away from the longitudinal axis of the probe 109. Despite having closely spaced adjacent blades, this cranked probe arrangement allows the ultrasound energy to be directed normally to the surface of the blade 450 using the five degrees of motion (three translational axes X, Y, Z and two rotary axes A,B) provided by the CMM and rotary head. Some geometries and scanning regimes may, however, benefit from providing a further rotational axis (C) around the primary probe axis for seamless continuous scanning.

Referring to FIGS. 15A, 15B, 15C, and 15D, the A-scan waveforms generated during thickness measurements of a planar part taken using a modular ultrasound probe having a coupling module comprising a hydrophilic elastomer sphere are illustrated.

FIG. 15A depicts a hydrophilic elastomer sphere tip 462 of a modular ultrasonic probe 464 being moved normally towards a planar inspection surface 466 by the CMM on which it is carried. The A-scan illustrated in the graph of FIG. 15A shows the amplitude of the received (returned) ultrasound pulse echoes as a function of time prior to the probe making contact with the surface. The first peak 470A corresponds to the excitation pulse generated by the transducer of the probe. The later peaks 470B, 470C are the time delayed internal reflection peaks from within the uncompressed hydrophilic sphere. These consistent A-scan waveforms of FIG. 15A thus show a "rest-state" condition from within the undeflected coupling module when it surrounded only by air. That is, the probe tip (i.e. the hydrophilic elastomer sphere 462) is yet to contact the inspection surface so there are no external mechanical forces acting on the sphere. A train of such A-scans can be performed at a high repetition rate (e.g. 1000-2000 Hz). As with the A-scan for a delay line transducer illustrated in FIGS. 2A and 2B, it is noted that the time window defined between the first and second peaks 470A and 470B provides the primary measurement window for the probe. The repetition rate should, however, not be so high as to cause significant interference between successive pulses.

FIG. 15B depicts the exact point at which hydrophilic sphere tip 462 of the probe 464 first comes into contact with the planar inspection surface 466. Even though there will be no noticeable shape distortion of the sphere at the instant of very first contact, a clear and immediate change in the measured A-scan waveform occurs. Firstly, the reflection peaks 480B and 480C (i.e. the time delayed internal reflection peaks from within the uncompressed hydrophilic sphere) show a reduction in peak amplitudes. This is more pronounced for the second reflection peak 480C. Secondly, as the probe begins to make a more significant contact, the peaks begin to shift marginally to the left (i.e. towards the t=0 excitation pulse 480A). Thirdly, even with light contact between the hydrophilic sphere 462 and the hard inspection surface 466, a plurality of measurable reflection peaks 482A, 482B and 482C from successive back wall reflections of the part can be observed within the primary measurement window of the A-scan.

It should be noted that only three reflection peaks 482A, 482B and 482C are shown in FIG. 15B for clarity (i.e. there are likely to be more than three such reflection peaks) and that these back wall reflections arise due to the coupling properties of hydrophilic spheres. In particular, an important benefit of the hydrophilic sphere based ultrasound probe is that it can provide sufficient delay for thin part measurement whilst only requiring modest probe contact with the inspection surface. This is a direct consequence of the ability to fill the air gap between the probe and the surface on account of the soft conformal contact properties of the hydrophilic sphere and their partially wet to the touch feel.

The change in the A-scan that results from contact with a surface thus allows the ultrasound probe to make surface contact measurements. This will be explained below in more detail. Although the back wall reflections 482A-482C may be adequate to provide a Mode-3 thickness estimation, it is preferred to load the ultrasound probe further onto the inspection surface in order to establish increased acoustic coupling with the part. In particular, further loading allows optimal coupling contact (also referred to herein as the coupling 'sweet spot') to be obtained; this optimal coupling is revealed by the combination of reduced reflection peaks from within the coupling module and increased back wall reflection peaks.

FIG. 15C shows the consequence of such further loading of the hydrophilic sphere 462 of the modular ultrasound probe 464 on to the inspection surface 466. As can be seen from the A-scan plot, the reduction in the amplitude of the coupling module reflection peaks 490B and 490C (i.e. the time delayed internal reflection peaks from within the uncompressed hydrophilic sphere) is more pronounced. This is accompanied by a noticeable increase in the SNR of the back wall reflections of primary interest to the thickness measurement (i.e. peaks 492A, 492B and 492C). It can also be seen that both the internal coupling module reflections (i.e. peaks 490B and 490C) and the back wall reflections (i.e. peaks 492A, 492B and 492C) within the measurement window are further shifted in time towards the t=0 transmit pulse 490A as the probe is loaded further on to the surface and the sphere becomes progressively more deformed. However, the delay between the successive back wall reflections (i.e. peaks 492A, 492B and 492C) is unchanged.

FIG. 15D shows further loading of the probe onto the surface past the "coupling sweet spot" mentioned above. There is often observed a further reduction in amplitude of the coupling module reflection peaks 500B and 500C (i.e. the time delayed internal reflection peaks from within the uncompressed hydrophilic sphere) but no substantial change in the back wall reflection signal (i.e. peaks 502A, 502B and 502C). The peaks of interest can also be seen to be further shifted towards the initial Transmit pulse at T=0 (i.e. main excitation peak 500A). Further loading of the probe onto the surface, beyond the "coupling sweet spot", thus gives no further improvement in the SNR of the back wall reflection signals. In addition, such further loading means that the sphere deformation can approach a condition in which temporal overlap between the transmit and receive waveforms of interest is observed within the A-scan or the hydrophilic sphere is damaged.

The A-scan data illustrated in FIGS. 15A to 15D can be subjected to a variety of signal or data processing methods to allow automatic detection of variations in a continuous train of A-scans whilst the probe is being maneuvered on to an inspection surface. Waveform information extracted from these A-scans, and in particular the transient waveforms from internal reflection echoes from the hydrophilic sphere, provides a sensitive and robust method for detecting exactly when the tip of the ultrasound probe makes contact with any other body. This surface contact information has several uses.

A first detection method involves capturing a single reference A-scan with the probe positioned at some 'null' position within the CMM volume when it is known that the tip of the ultrasound probe is not in contact with a solid body. This reference waveform (such as the waveform illustrated in FIG. 15A) only contains internal reflection peaks from the uncompressed sphere and represents a condition defined by no tip contact. Importantly, due primarily to the very high elasticity of the soft coupling sphere, it is observed that this A-scan waveform shape is consistently returned after any tip contact loading from any solid body has been removed. The A-scan segments containing the coupling module reflection peaks (i.e. the internal reflections from the hydrophilic sphere) can be extracted and repeatedly compared or differenced against the same time-gated segments from a continuous train of A-scans measured as the probe is maneuvered prior to surface contact. Monitoring for differences in this manner can be used to automatically detect when tip contact with an object occurs.

Automated detection decisions can be indicated based upon any suitable detection criterion. Although some scenarios for the probe could dictate a more sophisticated or adaptive detector (e.g. CFAR, Bayesian detectors), a simple square-law energy detector with an absolute pre-determined hard detection threshold can suffice in many scenarios. This approach is valid because the continuous train of measured A-scan waveforms exhibit quite negligible measurement-to-measurement variability whilst the probe is being maneuvered in free space at any speed or through any complex movement that the CMM and/or head can induce. Moreover, any contact between the probe tip and a solid body induces instantaneous and quite large changes across the observed internal reflections echoes from the hydrophilic sphere. The automated contact detection algorithm within the probe may also analyse any number of reflection echoes beyond the first echo return. For example, the $2^{nd}$ and $3^{rd}$ reflection waveforms can often change more noticeably in amplitude than the initial first echo return on such contacts (e.g. as seen in FIG. 15B) and thus these waveforms can also provide a sensitive indication of any touch contact event. The pulse generation repeat rate is preferably selected so that interference from previous pulses is minimised.

The signal features that define the coupling module internal reflection echoes which are extracted from each A-scan and used as the input data within the detector may simply be related to differences in accumulated waveform energy. However, it is noted that the signal metrics employed may vary in their ability to affect robust yet sensitive real-time tip contact detection. Other waveform metrics including peak voltage, signal kurtosis (i.e. fourth statistical moment), RMS, FFT and AR coefficients could equally-well be used, although any signal features can be extracted for use within the detector. Any such algorithms for detecting meaningful variations in the A-scan waveform in order to infer tip contact events will, in practice, require minimal computation as the comparison or detection decision based upon a differencing process need only be computed across the short time-gated segmented windows extracted from within each A-scan containing the coupling module internal echo peaks. Thus, in practice, the rate at which the probe can report tip contact status is more fundamentally limited by the frequency at which the A-scans can be generated, rather than detector computation. It should be noted that the A-scan generation rate depends upon the thickness and L-wave sound speed of the medium within the coupling module and the resulting transit time needed to record at least the first two reflections from the hydrophilic elastomer tip. Due to the relative simplicity and low computation in the detection task, the frequency at which contact status information can be reported by the probe and sent to peripherals (e.g. the CMM or measurement head controller) can be relatively high (e.g. up to 2000 Hz). However it is noted that increasing the repeat rate so that a new transmit pulse is induced before the previous reflections have more significantly attenuated can cause a set of additional unscheduled/spurious noise peaks of diminishing amplitude to proliferate into successive A-scans. These can be more significant in amplitude between the transmitted pulse and the first internal reflection, although they can be effectively filtered out within the primary measurement window using the primary signal processing method for extracting the required time delay between successive back wall reflections.

Generating tip contact status data at such a high rate allows the automated inspection system to respond or mechanically react relatively quickly to any unscheduled tip contact events that the probe may encounter unexpectedly during any type of movement induced by the automation platform (e.g. motion of the CMM and/or measurement head). For example, if a tip contact were to be detected whilst the probe was travelling along a linear trajectory at a typical scanning speed (e.g. 100 mm/sec), the minimum possible travel into the obstruction, assuming no latency in sending the interrupt command to the CMM and head to stop the movement, would equate to a deflection in the soft coupling element of the coupling module of only about fifty microns. Even allowing for some reasonable time latency in affecting the command for the CMM and/or measurement head to halt such a movement, the likely amount of deflection within soft coupling element of the coupling module would be orders of magnitude within the nominal maximum allowable deformation before which any damage to the hydrophilic sphere tip or rigid probe would be induced. The combination of high temporal resolution contact status data and the positional tolerance provided by the soft-elastic tip thus dictates a low probability of the occurrence of significant undetected impact damage to the probe tip.

As explained above, the sensitive touch contact capability is very useful for navigation of the probe within CMM space. This is especially since the probe is a rigid body and has no other sensing modality so could be easily damaged. However, the ability of the ultrasonic probe to generate useful surface interaction data at a very high rate goes beyond simple binary contact detection. As will be described below, signal and data processing methods have been devised that allow the probe to be used within any inspection as a simple yet sensitive touch probe capable of generating Cartesian point-cloud measurements describing the external form of an inspection part. This basic touch point capability has direct benefits to the metrology inspection conducted by the ultrasound probe (e.g. time saving) as well as wider applications (e.g. sensitive and accurate measurement of soft gelatinous parts with difficult optical properties that could not be measured easily with a conventional touch probe or an optical scanning probe). In addition, the loading condition of the probe against the inspection surface can be continuously estimated by direct exploitation of the internal coupling module delay echoes within the measured A-scan. This has direct and important benefits for both more controllable point measurements and continuous move scanning inspections undertaken using the ultrasound probe.

It should be noted that the touch capability could be further refined by exciting the probe's piezoelectric active element with a continuous sinusoid signal during manoeuvres. For example, the hydrophilic sphere tip could be driven with a continuous sinusoidal excitation at the resonant frequency, say 20 MHz. Any dampening detected in the resonance when the sphere is contacted by any solid could be detected.

Processing methods will now be described with reference to FIGS. 16 to 19 that allow the modular ultrasound probe to be used as a basic touch trigger probe that can take useful point cloud measurements across the external form of an inspection part. For example, this would allow the probe to adequately survey the orientation of a surface for a subsequent thickness measurement at a point by taking three touch measurements in close proximity around the required measurement node so as to estimate the surface normal. As described above, touch contacts may be detected with the probe by continuous monitoring of the internal reflections from the hydrophilic sphere of the coupling module so that any meaningful variation in these echo waveforms (e.g. Peak amplitude, Phase, time-of-arrival changes) from the calibrated non-contact reference condition can be detected.

FIG. 16 illustrates a modular ultrasound probe 546 moving at a constant velocity towards a solid block 547 with the probe tip 548 kept at a constant Z height with linear movement in both X and Y coordinates. The ultrasound probe 546 has a tip 548 that comprises a hydrophilic sphere. The modular ultrasound probe 546 is mounted to a CMM for movement, as described above with reference to FIG. 3.

The XYZ position of the probe tip (i.e. the position of the centre of the hydrophilic sphere) in the coordinate system of the CMM is collected via the CMM controller at a high data rate (e.g. 1000-2000 Hz). This tip position data is combined with a suitable signal generated by the ultrasound probe at the same rate that indicates if any significant perturbation in the hydrophilic sphere's internal reflection echoes are present thereby indicating the sphere has made contact with an object. This signal, which is analogous to the trigger signal generated by a touch trigger probe, could be generated by monitoring the absolute difference between the $2^{nd}$ internal reflection peak voltage (Vp) within each measured A-scan and a stored "no contact" reference A-scan as described above with reference to FIGS. 15A to 15D.

A touch event detected by the ultrasound probe thus causes the probe to issue an immediate instruction to the CMM (e.g. via a change in state of a trigger signal line) which is used to stop CMM motion and store the point measurement. There will, however, always be some latency associated with delivery of the instruction from the probe to the CMM and also a period of CMM deceleration is unavoidable. The delay in halting motion of the CMM causes the soft tip of the ultrasound probe to deform into the solid block so that its position when it comes to a complete stop may be significantly away from the point P on the surface where contact was first detected.

FIGS. 17A and 17B illustrate the above described effect. FIG. 17A shows the point P where contact is initially detected and FIG. 17B shows the further movement into the surface (i.e. to point O) that occurs before the ultrasound probe is brought to a halt. A close approximation to the point P could be made from interpolating the positional and trigger signal data time series acquired up to this point. Alternatively, if the probe is travelling at a relatively high speed when the touch event occurs, a more accurate result can be achieved with a back-off movement at a slower speed. This could involve removing the probe from the surface in the opposite direction to the approach vector but at a slower speed.

FIG. 18 shows plots of X-position 550, Y-position 552, Z-position 554 and trigger signal (Vp) status data 556 as a function of time during a move of the probe into and then away from the surface in the manner described above. The time series plots show the time of contact 558 and the time contact is lost 560 as dashed lines. The probe is thus moved into contact with the surface and comes to a halt at point O. There is then a short dwell period (which ends at point D) where the probe is stationary, before a slower back-off move is initiated. This slower reverse move allows a higher density of spatial measurement points to be recorded and the temporal quantisation error from detecting the time at which Vp returns to the reference level thereby indicating the contact has been broken has less influence upon the spatial quantisation error in estimating the XYZ position of P (i.e. due to the shallower gradients). During the slower linear back-off movement, it would also be possible within the probe hardware to generate the trigger signal (e.g. the Vp signal) from the A-scan data at a higher rate than the probe position is reported. This would allow a more precise estimate of P to be obtained by interpolation. More refined interpolation methods could also be employed that accommodate the subtle differences in reflection peak variations where contact deformation in the sphere occurs at different locations on the spheres and at different grazing angles.

The elastic hydrophilic spheres of the above described coupling modules may be synthesised to release differing quantities of water during an inspection. Releasing higher quantities of water (e.g. for lubrication across rougher surfaces) has been found to reduce the accuracy of any touch contact measurements taken during a back-off move. This is because a small droplet of water of varying size can accumulate around the location of the deformed sphere that causes a temporary physical bridge between the sphere and the inspection surface during the back-off move. This water droplet can introduce variability into when the ultrasound data indicates contact with the object is lost. Such variability can be easily overcome by not utilising the initial back off movement to take the touch measurement, but instead incorporating a second movement into the surface (e.g. along the same vector at the slower speed immediately after the initial back-off movement) in order to take the touch position data.

The use of the ultrasound probe to also acquire surface contact measurements has the additional benefit of being quicker than exchanging the ultrasound probe for a conventional surface contact (e.g. scanning or touch trigger) probe.

Referring to FIG. 19, it is also noted that due to the symmetry of the sphere only differences across latitudes (e.g. α and β) need to be considered. This is so long as the relationship between deformation and X Y or Z probe position of probe is linear or can be calibrated via intentional surface contact touches.

In addition to analysing the A-scans of the ultrasound probe to establish when surface contact is first attained, signal and data processing algorithms for estimating the probe loading and thus coupling condition during an inspection can also be included in the probe. For simplicity and because it is most relevant to how the probe may typically be used, scenarios where the probe is loaded into the inspection surface from a nominally normal direction will now be described. However, the same principles and methods can also be applied when loading the probe at angles that depart from the direction of L-wave travel (i.e. the axial direction of the transducer).

As already described with reference to FIGS. 15A to 15D, loading an ultrasound probe with a hydrophilic sphere tip against a surface induces measurable changes to the internal reflection echoes within the A-scan that relate to the normal deformation or Z-displacement within the sphere. As also described above, monitoring the peak amplitude (Vp) and/or the time of arrival (TOA) of the $1^{st}$ and $2^{nd}$ internal sphere echoes can thus be used to assess loading. In some cases, it is noted that a single combined metric related to the internal reflection echoes can be sensitive and robust enough for both contact detection and loading deformation estimation from calibration data (e.g. using a ratio of higher order reflection peaks).

FIGS. 20A and 20B illustrate an example of how the TOA and Vp, respectively of the first and second internal reflection peaks from the hydrophilic sphere of the ultrasound probe can change as the probe is gradually loaded normally on to the inspection surface at a constant slow speed (i.e. as the normal deformation of the hydrophilic sphere is gradually increased). It can be seen from the graphs of FIGS. 20A and 20B that the relationship between the Z-deformation (or Z-deflection) in the soft sphere and the TOA and Vp of the $1^{st}$ and $2^{nd}$ reflection peaks are substantially linear.

This consistent and repeatable relationship between metrics defining the shape and/or position of the internal sphere reflection echoes within the A-scan and the amount of sphere deformation induced by probe loading can be usefully compiled during calibration. In other words, data as illustrated in the plots of FIGS. 20A and 20B can be generated by probe loading measurements taken from an appropriate calibration artefact; e.g. the artefact described above with reference to FIGS. 13A and 13B. Such known (i.e. by calibration) relationships can be used directly during any subsequent inspection to estimate the deformation or loading condition of the probe by extracting the same signal features from the relevant peaks (e.g. TOA, peak amplitude) within each measured A-scan. For example, a comprehensive set of calibration loading measurements can be taken using the calibration block with the probe tip set at a range of set angles relative to the surface and a range of linear angles of arrival on the surface (i.e. at different grazing angles). Such a comprehensive loading calibration is practical for a symmetrical probe as the compiled relationships between loading vector and the chosen internal reflection peak features is the same irrespective of the initial axial rotation of the probe. Equipped with the set of calibration data related to deformation of the spheres, any new set of reflection peaks from an A-scan measurement can be classified to infer the deformation displacement either by interpolation (linear or non-linear curve fitting) or simply a Euclidean nearest-neighbour classifier.

It should be noted that the accuracy achieved in determining such loading conditions may vary. The most robust and accurate estimations of the loading of the probe in terms of deformation of the soft conformal tip (in mm) will thus typically be achieved where the L-waves are projected normally to the inspection surface along the probe axis. Fortunately, this is the most typical thickness measurement scenario where the part has parallel front and back walls.

In addition to acquiring individual measurements, continuous acoustic scanning inspections are possible, for example, across simple geometries such as a continuous solid form with parallel front and back walls. Such continuous scanning is preferably performed with an ultrasound probe comprising a hydrophilic elastomer sphere that is loaded against the inspection surface in a direction normal to the surface. Such continuous scanning is possible because of the self-lubricating action of the hydrophilic spheres and the ability to use loading estimations provided by analysis of the internal reflection echoes.

FIG. 21 depicts a scanning scenario in which a modular ultrasound probe 600 having a tip comprising a hydrophilic sphere 602 tip is scanned across an unknown, undulating inspection surface 604. The probe continuously acquires A-scan measurements and from each A-scan it estimates the Z deformation (Zd) in microns. This can be performed at a relatively high rate so that any sudden changes in the loading condition may be immediately evident within the Zd time plot, as shown.

As indicated in FIG. 21, the probe is moved laterally across the surface from a start point 606 to an end point 608. The probe is initially at a constant height (i.e. a constant z-height) above the horizontal surface and is loaded at a constant level within the "coupling sweet spot" region that corresponds to a constant Z deformation (Zd) or constant sphere tip displacement. When the probe first reaches the undulating region 610 that has an increased Z height, the Zd estimation initially increases without any deviation in the probe's Z-position. However, it is highlighted that the Zd estimation data may be used directly within the control loop of the CMM system to alter the probe height in response to the measured change in Zd. As shown by the lower graph of FIG. 21, the CMM may be adapted to provide real-time adjustment of the probe's height (i.e. Z position) in response to the Zd measurement. In this example, this is done by moving the probe upwards in proportion to the increase in Zd. This backing-off (in Z) of the probe thus results in the Zd value quickly returning to its mean (optimum) loading condition. Similarly, when the probe reaches the reduced high surface, the reduction in Zd can be immediately compensated by the CMM in order to lower the probe back down towards the surface.

This technique thus uses the internal reflection echoes from within the soft coupling layer of the hydrophilic sphere to directly, and in near real-time, ensure an optimal acoustic coupling condition. Such direct real-time estimation and thus control of probe loading conditions (i.e. using feedback control to the automation platform) against the inspection surface by interpreting the reflected L-waves within the coupling module not only has benefits to probe positioning and scanning, but also fundamentally affects the transmitted L-wave from which useful thickness measurements are made. It is noted that the highly elastic and conformable coupling elements also provide an inherent ability to vary and/or precisely control the projected L-wave beam entering the part by either controlled variation in normal loading displacement or re-orientation of the axial probe vector away from the inspection surface normal, in accordance with both fundamental laws of acoustic diffraction and refraction respectively. This proactive beam manipulation is most practical and effective when the probe is attached to a high precision automation platform, such as the CMM described with reference to FIG. 3.

FIGS. 22A, 22B, and 22C illustrate some of the ways in which an ultrasound probe having a hydrophilic sphere tip can be used to induce more precise control of the projected L-wave into objects. In particular, such a probe allows more complex internal geometries to be probed with ultrasound through either diffractive beam divergence control, by more precisely calibrated normal loading of the probe (i.e. varying the aperture size) or through refractive beam-steering control by precision re-orientation of the transducer axis.

FIGS. 22A and 22B illustrate how increased loading of an ultrasound probe 620 with a hydrophilic sphere tip 622 can induce a wider diameter aperture on the inspection surface producing a collimating effect that reduces the naturally divergent beam width. As shown in FIG. 22B the narrower beam is beneficial since it avoids internal features 624 in the object being inspected that could otherwise result in spurious reflection echoes interfering with the measurements of interest.

Referring to FIG. 22C, an object having non-parallel front and back walls can be measured by re-orientation of the probe 620 away from the surface normal. Such beam-steering may be limited to only small refraction angles to reduce mode conversion effects. For such small angles the slower shear wave mode is less significant or it can be time-gated out of the A-scan.

A wide variety of variants to the ultrasound probes described above are possible. For example, a plurality (e.g. 15-20) of hydrophilic spheres could be cascaded together to form a continuous chain of touching spheres within a correspondingly long absorbent shell. The first sphere could be positioned within the shell so as to make contact with a transducer wear plate and the final sphere in the chain could protrude from the shell so as to contact the inspection surface. Such a probe design would permit more remote inspection regimes where it is undesirable or physically impossible to position the transducer probe tip close to the measurement node on the inspection part. The useful application of such variant designs is possible because of the extremely low L-wave attenuation properties observed in such hydrophilic media components. This results in negligible propagation loss from the transducer to the coupling module tip.

In addition to such constructions offering an extremely efficient acoustic waveguide for the inspection L-wave, it is also possible to manipulate the projected L-wave within a coupling module. Most notably, scenarios can arise where the L-wave inspection may need to be conducted along some axis other than the normal probe axis (e.g. for measurement in confined spaces). For example, it would possible to embed an acoustic reflecting mirror within a chain of hydrophilic sphere that simply re-directs the L-waves in some known direction, in line with the laws of acoustic reflection (i.e. angle of incidence equals the angle of reflection). Such a reflecting mirror is simply a flat acoustically reflecting surface (e.g. with a high acoustic impedance) mounted at a set angle.

FIGS. 23 to 25 illustrate a selection of different scenarios in which a cascaded chain of hydrophilic elastomer spheres can be usefully applied.

FIG. 23 illustrates how a cascaded chain of hydrophilic elastomer spheres 640 can be used to inspect the bottom of a long and narrow hole. As indicated by the illustrated A-scan, it is noted that the primary measurement window for a probe comprising such a chain of spheres becomes shifted in accordance with the number of spheres within the chain. However, the resulting back wall reflections within the A-scan are measureable and have a SNR approaching that achieved with a single sphere.

FIG. 24 illustrates that the spheres can be sized so as to form a tapered chain of spheres 650. The chain of spheres 660 can also be accumulatively bent off-axis using weak diffractive effects. Again, the resulting back wall reflections within the A-scan are measurable and have a SNR approaching that achieved with a single sphere.

FIG. 25 shows a chain of hydrophilic spheres 670 that comprise a reflecting mirror 672 for inspections perpendicular to the probe/transducer axis. Such an ultrasound probe can be useful for comprehensive metrology inspection within tubes and/or containers where the probe can be rotated around the circumference of the enclosure.

Ultrasound probes may be provided with different (non-spherical) shapes of hydrophilic elastomer hydrated within a matching absorbent shell. In addition to the basic spherical shape described, super absorbent polymers or lightly cross-linked vinyl elastomers with a high water content (e.g. typically 75-95%) can be synthesised so as to grow into practically any closed-form continuous shape that is required when hydrated, e.g. so as to fit perfectly inside the outer absorbent shell. A variety of bespoke (e.g. longer and/or thinner prismatic) shapes of continuous hydrophilic elastomer material within matching PTFE shells can be designed to accommodate any complex geometry part. By observing the A-scan from such coupling elements, it is evident that the back wall reflections reside in the much wider first measurement window. It is also noted that the various methods by which the internal reflection echoes within the coupling module are processed to estimate loading displacement or contact status also hold for such alternative designs.

As explained above, a compound class of coupling modules may be provided that do not comprise a hydrophilic sphere. FIGS. 26A, 26B, 26C, and 26D illustrate the A-scans generated from an ultrasound probe with a compound class of coupling module, for example as described above with reference to FIG. 7. As can be seen by comparing FIGS. 26A to 26D with FIGS. 15A to 15D, there are differences in the signal that is generated with a compound class of coupling module and hence different processing can be used to interpret the A-scans and extract information useful to the contact detection, loading, scanning and accurate thickness measurement processes.

FIGS. 26A to 26D show an ultrasound probe 700 with a normal beam compound coupling module comprising a latex rubber tip 702 loaded on to a simple inspection surface.

FIG. 26A shows the probe 700 approaching a surface. Prior to making contact with the surface, it can be seen that the A-scans incorporates only evenly spaced repeated reflections (i.e. first, second and third delay line reflection peaks 701, 703 and 704) from the rigid plastic delay line element 704, after the initial Tx pulse (not shown in the figure). These reflections show negligible measurement to measurement variability whilst the probe moves through free space within the CMM volume.

Referring to FIG. 26B, when the latex rubber probe tip 702 comes into contact with the surface, there is an immediate variation in the measured A-scan response. This initial tangential contact induces no visible shift in the time of arrival of the internal reflection echoes, yet induces quite an obvious reduction in the 2nd and 3rd reflection echo amplitudes (i.e. peaks 710 and 712). Depending on the coupling performance (e.g. defined by surface finish soft coupling and the part geometry), this reduction in reflected energy occurs in conjunction with increased back wall reflection waveforms 714 from energy transmitted into the part.

Referring to FIG. 26C, as the probe 700 is loaded further on to the surface the soft coupling layer (i.e. the latex rubber tip) deforms so the rigid planar delay element comes into closer conformal contact with the surface. The amplitude of the 2nd and 3rd reflection echoes (i.e. peaks 720 and 722) reduce further and there is an increase in the amplitude of the successive back wall reflections (i.e. peaks 724). However, this reduction in peak amplitude for the delay line peak signals (i.e. peaks 720 and 722) is not accompanied by any change in the time of arrival (TOA) or phase of these reflection peaks. Moreover, as highlighted by FIG. 26D, withdrawing the probe entirely from the surface causes the delay line peaks to return to the same levels and adopt the same shape as before the surface contact was made.

FIG. 27 depicts how the time of arrival and the peak amplitude of the first and second delay line reflection peaks for the probe described with reference to FIGS. 26A to 26D evolve as the probe is loaded linearly on to the inspection surface. In particular, FIG. 27 shows that the reflection peaks from the rigid delay medium remain fixed in time relative to the T=0 excitation within the A-scans. Loading calibration is thus more effective using waveform features that quantify the proportion of acoustic energy that can leak from the rigid delay medium with increased loading condition (e.g. ratios of 2nd or 3rd order peak voltages Vp). However, it is emphasised that such plots can still be usefully compiled during a calibration procedure and used to automatically detect contacts (e.g. through a hard threshold energy detector) or classify loading conditions (e.g. through linear or polynomial interpolation from the plots or some other computationally efficient classifier).

A signal processing method for generating thickness measurements from the measured A-scans within the measurement window will now be described. Any such signal processing algorithm is preferably robust and may be based upon a form of generalised cross correlation or replica correlation to extract accurate time delays between first, second and possibly third back wall reflections. It should be noted that beyond the third back wall reflection, waveform dispersion can start to affect the time difference estimation accuracy due to perturbations in the fine-scale shape of the return.

A preferred signal processing approach employs a form of replica correlation processing. This technique allows robust, computationally efficient and accurate time-delay estimation. In particular, a cross-correlation algorithm with spectral pre-whitening retains accuracy better than conventional amplitude threshold time of arrival methods. Although a replica correlation process is preferred, it should be noted that other techniques could be used. For example, a square-law amplitude threshold detector could be used in which reflection peaks are assumed to be detected at the point at which the waveform intensity or amplitude exceeds some set threshold. One dimensional edge detectors or wavelet decomposition techniques could also be used as they allow the required temporal accuracy to be maintained whilst smoothing noise. However, cross-correlation algorithms are better suited to high-frequency real-time implementation.

Referring to FIG. 28, the function of a replica correlator is schematically illustrated in which the absolute time delay between successive back wall reflections can be estimated with an accuracy that approaches the fundamental measurement resolution provided by the digital acquisition system (e.g. a time equating to the reciprocal of the ADC sample rate). A replica correlator is a form of matched filter where the output is computed from the cross-correlation between the measured A-scan and a delayed replica of a backwall reflection.

In particular, FIG. 28 illustrates how the replica correlation process involves correlating the time-windowed A-scan response y(n) with one or a bank of stored or extracted back wall reflection waveforms x(n). This correlation process is implemented by transforming the input waveforms x(n) and y(n) to the frequency domain using first and second DFT algorithms 750 and 752 respectively. The first and second DFT algorithm algorithms 750 and 752 may comprise any suitable form of the well know FFT algorithm. A multiplicator 754 then performed successive multiplication operations in the frequency domain on the transformed signals. The output of the multiplicator 754 is converted back into the time domain by a third DFT algorithm 758 and a peak detector 760 outputs data to a delay estimator 762. When using the favoured phase transform version of the generalised cross-correlation (GCC-PHAT) algorithm, only the signal phase information is preserved after the cross-spectrum is divided by its magnitude. Ideally, with no additive noise, this processor approaches a delta function centred at an accurate time delay estimation.

Such a fast convolution process may suffer from inaccuracy when transforming the result back to the time domain due to spectral smearing and leakage. Therefore, a pre-whitening filter 756 is implemented in order to improve the temporal accuracy and SNR robustness of the time delay estimation process. Phase transform pre-whitening has the effect of equalising the cross spectra (Pxy) phase so as to maximise the SNR and temporal accuracy of the dominant delay against multipath reverberation. Although it can be most effective form of pre-whitening for A-scans measured with the probe, any such correlation method (e.g. Knapp and Carter) can be used. For example, the phase transform method may become less effective for low SNR environments.

Referring next to FIG. 29, the principle of the phase transform replica correlator algorithm is illustrated. In particular, this figure illustrates a measured back wall response from the measurement window being presented to the signal processing stage.

The repeated back wall reflections (i.e. peaks 780) within the measurement window exhibit strong correlation in terms of repeated shape, especially in terms of their phase. Although the signal level attenuates from the first reflection echo 780 to the third reflection echo 782, the SNR is still relatively high. As indicated, the measurement window response can be correlated with a stored replica of the back wall reflection echo using the phase transform version of the cross correlator (GCC-PHAT). This generates a correlation response 784 with some noise suppression (i.e. the correlation process induces some SNR gain) and effective sharpening of the waveform representing each echo at the exact time sample with a maximum phase correlation. From this, a simple maximum peak detector can determine the time sample of each echo and the time difference between these peaks (t1 and t2) represents the time delay from which the thickness estimations can be made. Although the replica waveform can be measured during calibration, it is also indicated that the same algorithm can be effective by extracting the back wall waveforms directly from the A-scan itself or by an auto-correlation version of the algorithm.

In general, the data processing employed to assess every measured input A-scan in order to simply detect tip contacts (e.g. by a hard threshold detector) and/or to quantify the deformation in the soft coupling module (e.g. Zd) in order to ensure optimal coupling requires less computation that the subsequent signal processing required to measure the thickness of the coupled part. Therefore, a practical feature of the probe is that it may function in more than one automated mode of operation.

FIG. 30 depicts a flow chart showing possible modes of operation, control and flow of data between the probe and the peripheral hardware. As shown, a probe movement command can be induced from the probe control software through the CMM/head controller with ultrasound A-scans being generated simultaneously at a high rate. As a matter of course, basic processing could extract ultrasound reflection peak features for every measured A-scan and assess, via a hard threshold detector, whether the tip is in contact with any object. If no contact is detected, the movement induced by the probe controller through the CMM/head controller can continue with more A-scans being acquired, but no other processing being executed on the probe.

It should be noted that the measurement resolution of the probe or apparatus when applying spectral correlation methods (e.g. the GCC) to determine the accurate time delay information from which the thickness of the contacting part can be directly estimated is typically limited by the digitising sampling frequency within the receiver electronics (i.e. the ADC). In situations where the reflection waveforms of interest are smooth predictable high SNR signals without significant stochastic transient components (e.g. bandlimited), it has been found to be possible to artificially increase the effective system resolution by regular interpolative up-sampling of the raw measured A-scan response and the replicas prior to applying the correlator. Moreover, depending upon the SNR and noise statistics of the measured A-scans, a selection of different pre-whitening filters (i.e. weighting functions in the frequency domain) can be applied within the signal processing to make more accurate thickness measurements. Such pre-whitening filters include the smoothed coherence transform, the Roth filter or the Hannah and Thompson filter.

It is also noted that the Phase Transform version of the GCC algorithm that is mentioned above may not always be optimal for lower SNR regimes, when used in isolation. For example, A-scans measured with the apparatus containing the back wall reflection and or internal delay line reflection signal of interest could also contain higher levels of electronic noise from the measurement system (e.g. in cases where no averaging is applied across A-scans or lower cost instrumentation is employed) or higher acoustic background noise within the sensing system measurement band (e.g. when measurements are taken using high acoustic noise assets or a high noise automation platform such as the crawler platform described below). The skilled person would thus appreciate how the most appropriate signal analysis technique may vary for different applications.

If contact is detected, the CMM/head controller can be immediately alerted, so as to report probe position at contact and/or induce some interrupt movement action. This contact detection could also automatically enable the probe to begin processing the ultrasound reflection echoes to quantify the ultrasound probe coupling deformation against the inspection surface (i.e. related to the "coupling sweet spot"). More A-scans could continue to be generated at a very high rate, still without any computationally intensive thickness measurement signal processing being activated, until the coupling contact (i.e. coupling Z-deformation) is deemed to be within the "coupling sweet spot" or the coupling deformation tolerance. Although this acceptable coupling condition would be determined primarily by the methods described, since it relates mostly to assessment of the soft coupling element (e.g. hydrophilic sphere), it could possibly include some basic assessment of back wall reflections in the measurement window (e.g. simple metrics such as kurtosis or peak amplitude etc).

Following automated qualification that the probe coupling is sufficient or optimised, the more computationally and time intensive signal processing algorithm within the probe could be activated to extract the successive back wall reflections within the primary measurement window of the A-scans and measure their time delay. For many scenarios, e.g. continuous scanning across a part, it may in practice be necessary for the probe to continuously execute the thickness measurement processing algorithm for every measured A-scan. In this way, the computationally efficient yet accurate time delay estimation method provides important operational benefits.

FIG. 30 thus represents one architecture for the probe in which a large proportion of the processing is accomplished by processing units (e.g. FPGA, DSP, CISP) within the ultrasound probe itself. This distributed processing architecture has advantages for deployment upon a CMM where communication channel bandwidths through the measurement head and scope for local memory storage on the probe can be limited. However, it is noted that there are other possible architectures and methods for processing the A-scan data. For example, in some cases, it may be possible to affect all of the rudimentary processing for contact detection and optimal coupling "on the fly" but record extended batches of A-scans locally in memory, for batch transfer and post-processing of the thickness measurement on some other processor (e.g. a laptop or PC). Regardless of the processing architecture, the basic signal processing indicated here to estimate the time delays via mode-3 gauging remain both robust and accurate.

Embodiments of the ultrasound systems described herein and the associated automated inspection concepts may be useful for internal metrology measurements within highly attenuating and much thicker metallic and non metallic parts than those described above. In particular, the ultrasound apparatus may be used to measure certain high value safety critical metallic parts (e.g. medical implants) that have been manufactured using additive manufacturing (AM) methods (e.g. using a selective laser melting machine). Such parts may require both internal metrology measurements and non-destructive gauging to ensure that the porosity exhibited across the part is within the required tolerance. This type of porosity measurement is becoming more important as such AM techniques can specifically design-in a variety of porosities across the part. It is highlighted that such porosity distribution estimation across an AM solid part of known or measured geometry may be adequately achieved by direct estimation of the sound speed distribution across the part. This is because a strongly linear and easily calibrated relationship exists between longitudinal sound speed and porosity. A linear relationship exists between the shear wave velocity and the porosity also. This could also be used in some circumstances.

The modular ultrasound apparatus described herein is also capable of focusing projected ultrasound at known depths or angles within a part (e.g. using a coupling module having a spherically focused planar-concave lens). The apparatus could thus be used for the automated detection, location and sizing of internal defects and voids within inspection parts.

The modular ultrasound probe mentioned above may advantageously be used for dimensional form measurements of soft material parts. For example, some softer solid gelatinous, organic or non-metallic parts may not be inherently suited to conventional contact probing as the surface interaction into such softer parts may not cause the probe stylus to mechanically deflect in a consistent manner (e.g. due to mechanical hysteresis effects) and/or such contacts could conceivable induce unwanted indentations in the soft parts under inspection. Such parts could include soft elastic or plastic polymer membranes, fabrics and leather, food stuffs and even organic membranes and human tissues.

Such soft metrology tasks could involve the soft coupling element within the probe being specifically selected to be softer than the object or material being inspected. This is so the coupling element deflects by a measurable amount before inducing any deflection within the part being inspected. An extremely soft hydrophilic vinyl polymer with a very high water content (e.g. 95%) could thus be provided as the coupling element of an ultrasound probe. Such a coupling module could be provided as one of a set of coupling modules.

The modular ultrasound probe mentioned above may advantageously be used for dimensional form measurements of high quality surface finish parts. In particular, it is further noted that some other precision manufactured rigid parts with complex geometries but with an extremely high quality smooth polished surface finish may require automated dimensional measurements. However, contact interaction between a hard ruby ball stylus probe and such polished inspection surfaces may not be ideal as such interactions could potentially induce some scratches or impact damage on the surface. Moreover, alternative non contact optical measurement probes (e.g. a laser scanning probe) may not be suitable due to the non conductive optical properties of the inspection surface (e.g. an optically transparent acoustic concave or convex lens or a parabolic optical mirror).

The modularity of the ultrasonic inspection apparatus described above and more specifically the inherent ability to automatically change and tailor the different coupling module designs to accommodate specific inspection conditions is particularly beneficial during the measurement of complex geometry parts. Moreover, the choice of any specific coupling module will often dictate the specific gauging methods employed to generate output measurements (e.g. thickness values across each measurement node).

For example, during the inspection of a typical hollow aerospace blade, a selection of different coupling module designs and associated gauging methods could be employed in succession for more comprehensive coverage inspections. Specifically, a large proportion of the part's bulk external surface may be parallel to the internal back wall surface. For such bulk "skin thickness" gauging, coupling modules that comprise a hydrophilic sphere may be attached to the ultrasonic probe and continuously scanned laterally across the blade with the probe retaining a substantially normal orientation to the inspection surface. Such normal incidence continuous scanning without the probe leaving the inspection surface utilises the self-lubricating property of this type of soft conformal and elastic hydrophilic coupling module, as previously described. It therefore facilitates a very high density of measurement points across the inspection surface via the mode-3 gauging method using the above described replica correlation method for robust time delay estimation at each node.

However, it is noted that the method for measuring bulk skin thickness is not necessarily appropriate for inspection across the entire blade. For example, in the vicinity of the leading and trailing edge of the blade aerofoil, the external front wall and internal back wall often depart from such a parallel geometry. In this instance, a refractive coupling module may be used to project ultrasonic L-waves in the required direction towards the internal back wall. This could involve using a coupling module having a fixed rigid delay line, with an appropriate refractive wedge angle. Alternatively, with appropriate calibration, the refractive inspection task could be accomplished using a coupling module having a hydrophilic sphere but with the probe orientated at the appropriate angle from the surface normal. In either case, mode-3 inspection becomes problematical because the non-parallel front and back wall surfaces prevent successive back wall reflections returning to the probe. Mode-2 gauging in which the time delay between the first delay line or internal reflection peak from the coupling module and the back wall is estimated, is also not appropriate as no strong internal reflection peak would exist at such a refractive angle. Therefore, in this case, mode-1 gauging (in which the absolute time delay between the initial excitation pulse and the subsequent back wall reflections is estimated) could advantageously be implemented instead.

To obtain the highest possible mode-1 thickness gauging accuracy, a further calibration procedure may be required in which a range of refractive measurements are made across a refractive calibration block machined from the same material as the inspection part and which incorporates one or more back walls at the same front wall and back wall orientation as the inspection part. In the same way as any such mode-1 calibration procedure, use of the same material in the calibration block as the inspection part allows the sound speed calibration to be integrated into this refractive angle calibration. That is, a separate sound speed calibration procedure can become unnecessary because a range of backwall time delays for known refractive thicknesses taken during calibration can mean that any further time delay measured with the probe during the inspection can directly infer the unknown thickness by a linear interpolation.

It is also possible to determine the speed of sound within the soft coupling element of a coupling module. Although such a sound speed measurement is by no means essential (e.g. it is not required for accurate thickness inspections of parallel eccentric parts such as airframe skins and parallel hollow blades using the mode-3 method), it does have some advantages. For example, the sound speed of the coupling layer within the attached coupling module may be affected slightly by atmospheric temperature variations and, for certain probe functions such as off-normal axis inspections of non-parallel front and back wall inspection parts, it can be beneficial to calibrate (i.e. measure) the sound speed of individual coupling modules within the inspection. More specifically, the sound speed of the coupling medium will directly affect the angle of projection of the ultrasound waveform into the inspection part, in accordance with Snell's Law of Refraction. Hence, a more accurate and calibrated measure of this absolute sound speed within the homogeneous isotropic coupling medium can be beneficial for building up and projecting the exact position and orientation of internal reflection surfaces.

The measurement of a coupling element's sound speed can also have alternative applications; e.g. classifying unknown liquid samples that interact with the coupling element. The speed of sound of the coupling module (CL) could be derived by direct measurement of the longitudinal dimensions (d) of the coupling medium and estimation of the roundtrip time of flight (t) (i.e. using the relationship CL=2*d/t) via mode-1 mode-2 or mode-3 methods. Alternatively, a method could be used that involves linearly loading the probe in a highly controlled and precise fashion on to a known planar surface. More specifically, it has been found that measurement of the change in time of arrival (TOA) of the first internal reflection waveforms from the coupling layer as the probe is loaded on to a planar surface allows the linear relationship between this TOA and the coupling layer deformation (i.e. the linear loading displacement) to be compiled. From this linear relationship plot (i.e. for a incompressible coupling layer), the sound speed can be calculated directly as the gradient. In other words, the absolute gradient between the TOA(t) Vs Z-deformation or loading (r) equates to half the sound speed (CL) from the relation r=(CL*t)/2. This method has been found to be accurate and ensures that no potentially inaccurate estimation of the exact heuristic longitudinal dimension of the coupling layer is required to calculate the coupling layer sound speed.

Although it is described above how the ultrasound apparatus can be installed on a bridge type CMM, it should be noted that it can be used with other apparatus.

FIG. 31 illustrates how the ultrasound probe 802 described above can be mounted on an x-y scanner 800.

FIG. 32 illustrates how the ultrasound probe 802 described above can be mounted on an ultrasonic crawler system 810 for measuring internal cracks and corrosion within thin aerospace structures (e.g. the fuselage skin). In such an embodiment, strong reflection echoes that occur in the A-scan between the back wall reflections can be detected as additional unwanted interfaces within the part volume that may be classified as an internal void or crack.

In such an embodiment, the crawler vehicle 810 may implement continuous scanning over a large curved structure to measure the internal thickness of the structure's skin (e.g. an aerospace structure or wind turbine blade). However, the curvature of the part and its interaction with the crawler wheels may induce some variability in the exact clearance between the mobile platform upon which the ultrasonic probe is mounted and the inspection surface. By high resolution estimates of the current deflection (Zd) in the soft coupling tip, it is possible to adapt the Z position of the probe relative to the platform as it travels along the part to compensate for the variable clearance, thus retaining the probe deformation within a set tolerance (i.e. the 'coupling sweet spot'). In its simplest form, adaption of the probe height relative to the platform in response to variation in the soft coupling element deformation could be implemented using a linear stage motor with a simple linear encoder attached to the platform that would allow the Z-height of the probe to be varied in real-time during the inspection. In a more sophisticated embodiment, a second rotational motor and encoder may be incorporated allowing the probe to be rotated whilst remaining in the plane of its motion so as to alter its angle of incidence against the surface in response to changes in the surface normal.

The invention claimed is:

1. A method for inspecting an object using an ultrasound inspection device carried by a coordinate positioning apparatus, the ultrasound inspection device comprising an ultrasound transducer and a coupling element for contacting and acoustically coupling to the object to be inspected, the coupling element comprising a self-lubricating material, the method comprising:
   a scanning step in which the coupling element of the ultrasound inspection device is moved along a path on a surface of the object by the coordinate positioning apparatus while ultrasound measurements are acquired, wherein deformation of the coupling element is determined during the scanning step to provide a measure of a height of the ultrasound inspection device above the surface of the object.

2. A method according to claim 1, wherein the coordinate positioning apparatus is configured to move the ultrasound inspection device towards or away from the surface of the object during the scanning step in response to any change in the measured height.

3. A method according to claim 2, wherein the measured height is used in a control loop of the coordinate positioning apparatus to provide a real-time adjustment of the height of the ultrasound inspection device above the surface of the object.

4. A method according to claim 1, further comprising a step of using the ultrasound inspection device to measure a thickness of the object.

5. A method according to claim 1, further comprising steps of using the ultrasound inspection device in a pulse-echo mode and measuring a speed of sound within the coupling element by analysing reflections from within the coupling element when the coupling element is subject to a plurality of different deformations.

6. A method according to claim 1, further comprising a calibration step of measuring a speed of sound in a material of the object.

7. A method according to claim 1, further comprising a step of using acoustic energy reflected from the coupling element to assess a physical condition of the coupling element.

8. A method according to claim 1, further comprising a step of analysing internal reflections from the coupling element to determine when the coupling element makes contact with the object.

9. A method according claim 1, wherein the coordinate positioning apparatus comprises a rotary head to which the ultrasound inspection device is attached, the rotary head comprising at least two rotary axes.

10. A method according to claim 1, wherein the self-lubricating material of the coupling element comprises a hydrophilic elastomer.

11. A method according to claim 1, wherein the self-lubricating material of the coupling element comprises a super absorbent polymer hydrogel.

12. A method according to claim 1, wherein the coupling element further comprises a sphere of the self-lubricating material.

13. A method according to claim 1, wherein the ultrasound inspection device is a modular arrangement that comprises a base module comprising the ultrasound transducer and a coupling module that comprises the coupling element.

14. A method according to claim 13, further comprising a step of using the coordinate positioning apparatus to attach the coupling module to, or detach the coupling module from, the base module.

15. A method for inspecting an object using an ultrasound inspection device and a coordinate positioning apparatus comprising a rotary head having at least two rotary axes, the ultrasound inspection device being attached to the rotary head and comprising an ultrasound transducer and a coupling element, the coupling element comprising a self-lubricating material for contacting and acoustically coupling to the object to be inspected, the method comprising:

a scanning step of moving the coupling element of the ultrasound inspection device along a path on a surface of the object while acquiring ultrasound measurements of the object; and a step of determining a deformation of the coupling element during the scanning step to provide a measure of a height of the ultrasound inspection device above the surface of the object.

16. A method according to claim 15, wherein the coordinate positioning apparatus is configured to move the ultrasound inspection device towards or away from the surface of the object during the scanning step in response to any change in the measured height.

17. A method according to claim 16, wherein motion of the rotary head about the at least two rotary axes is used to move the ultrasound inspection device towards or away from the surface of the object during the scanning step.

18. A method for inspecting an object using an ultrasound inspection device carried by a coordinate positioning apparatus, the ultrasound inspection device comprising an ultrasound transducer and a coupling element for contacting and acoustically coupling to the object to be inspected, the coupling element comprising a self-lubricating material, the method comprising:

a scanning step in which the coupling element of the ultrasound inspection device is moved along a path on a surface of the object by the coordinate positioning apparatus while ultrasound measurements are acquired;

using the ultrasound inspection device in a pulse-echo mode; and measuring a speed of sound within the coupling element by analysing reflections from within the coupling element when the coupling element is subject to a plurality of different deformations.

* * * * *